US008770814B2

(12) United States Patent
McCollum et al.

(10) Patent No.: US 8,770,814 B2
(45) Date of Patent: *Jul. 8, 2014

(54) LIGHT EMITTING PANEL ASSEMBLIES

(71) Applicant: Rambus Delaware LLC, Brecksville, OH (US)

(72) Inventors: Timothy A. McCollum, Avon Lake, OH (US); Jeffery R. Parker, Richfield, OH (US); Robert M. Ezell, Brunswick, OH (US)

(73) Assignee: Rambus Delaware LLC, Brecksville, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/891,227

(22) Filed: May 10, 2013

(65) Prior Publication Data

US 2013/0314944 A1 Nov. 28, 2013

Related U.S. Application Data

(63) Continuation of application No. 13/313,462, filed on Dec. 7, 2011, now Pat. No. 8,459,858, which is a continuation of application No. 12/858,609, filed on Aug. 18, 2010, now Pat. No. 8,104,944, which is a continuation of application No. 12/429,226, filed on Apr. 24, 2009, now Pat. No. 7,780,329, which is a continuation of application No. 11/499,152, filed on Aug. 4, 2006, now abandoned, which is a continuation of application No. 10/601,616, filed on Jun. 23, 2003, now Pat. No. 7,108,414.

(51) Int. Cl.
*F21V 7/04* (2006.01)

(52) U.S. Cl.
USPC ............ 362/603; 362/613; 362/619; 362/625

(58) Field of Classification Search
USPC ......... 362/603, 604, 606, 612, 613, 617, 619, 362/620, 623, 625, 626, 231, 812; 40/546
See application file for complete search history.

(56) References Cited

U.S. PATENT DOCUMENTS

| | | |
|---|---|---|
| 2,071,239 A | 2/1937 | Birdsall et al. |
| 2,095,558 A | 10/1937 | Oberacker |
| 2,262,930 A | 11/1941 | Gasper |
| 2,374,323 A | 4/1945 | Bihr |
| 2,810,225 A | 10/1957 | Hardesty |
| 2,831,453 A | 4/1958 | Hardesty |

(Continued)

FOREIGN PATENT DOCUMENTS

| | | |
|---|---|---|
| CH | 438912 | 6/1967 |
| EP | 0 453 092 A1 | 10/1991 |

(Continued)

*Primary Examiner* — Thomas Sember
(74) *Attorney, Agent, or Firm* — Renner, Otto, Boisselle & Sklar, LLP

(57) ABSTRACT

An optical assembly comprises light sources and a light emitting panel member having an input edge to which each of the light sources is optically coupled at a different location along the input edge. Different sets of individual optical deformities on or in at least one of the sides of the panel member each have at least one surface that is shaped or oriented to extract light propagating in the same direction through the panel member in different directions for viewing from different angles through one of the sides of the panel member.

12 Claims, 16 Drawing Sheets

(56) References Cited

U.S. PATENT DOCUMENTS

| | | |
|---|---|---|
| 3,043,947 A | 7/1962 | Albinger, Jr. |
| 3,070,913 A | 1/1963 | Miller |
| 3,328,570 A | 6/1967 | Balchunas |
| 3,491,245 A | 1/1970 | Hardesty |
| 3,543,014 A | 11/1970 | Bustad |
| 3,571,585 A | 3/1971 | Schermerhorn |
| 3,590,509 A | 7/1971 | Fukumitsu |
| 3,665,626 A | 5/1972 | Lund et al. |
| 3,752,974 A | 8/1973 | Baker et al. |
| 3,761,703 A | 9/1973 | Mund et al. |
| 3,892,959 A | 7/1975 | Pulles |
| 3,906,650 A | 9/1975 | Coffman |
| 3,958,113 A | 5/1976 | Termohlen |
| 4,043,636 A | 8/1977 | Eberhardt et al. |
| 4,118,111 A | 10/1978 | Laesser |
| 4,177,501 A | 12/1979 | Karlin |
| 4,183,628 A | 1/1980 | Laesser |
| 4,257,084 A | 3/1981 | Reynolds |
| 4,271,408 A | 6/1981 | Teshima et al. |
| 4,282,560 A | 8/1981 | Kringel et al. |
| 4,290,093 A | 9/1981 | Thompson et al. |
| 4,310,219 A | 1/1982 | Jaccard |
| 4,385,343 A | 5/1983 | Plumly |
| 4,446,508 A | 5/1984 | Kinzie |
| 4,460,940 A | 7/1984 | Mori |
| 4,542,449 A | 9/1985 | Whitehead |
| 4,573,766 A | 3/1986 | Bournay, Jr. et al. |
| 4,630,895 A | 12/1986 | Abdala, Jr. et al. |
| 4,714,983 A | 12/1987 | Lang |
| 4,729,068 A | 3/1988 | Ohe |
| 4,729,185 A | 3/1988 | Baba |
| 4,751,615 A | 6/1988 | Abrams |
| 4,763,984 A | 8/1988 | Awai et al. |
| 4,765,701 A | 8/1988 | Cheslak |
| 4,791,540 A | 12/1988 | Dreyer et al. |
| 4,811,507 A | 3/1989 | Blanchet |
| 4,845,596 A | 7/1989 | Mouissie |
| 4,885,663 A | 12/1989 | Parker |
| 4,890,201 A | 12/1989 | Toft |
| 4,906,070 A | 3/1990 | Cobb, Jr. |
| 4,907,132 A | 3/1990 | Parker |
| 4,961,617 A | 10/1990 | Shahidi et al. |
| 4,974,122 A | 11/1990 | Shaw |
| 4,975,808 A | 12/1990 | Bond et al. |
| 4,978,952 A | 12/1990 | Irwin |
| 5,005,108 A | 4/1991 | Pristash et al. |
| 5,009,019 A | 4/1991 | Erlendsson et al. |
| 5,009,483 A | 4/1991 | Rockwell, III |
| 5,027,258 A | 6/1991 | Schoniger et al. |
| 5,036,435 A | 7/1991 | Tokuda et al. |
| 5,039,207 A | 8/1991 | Green |
| 5,050,946 A | 9/1991 | Hathaway et al. |
| 5,056,892 A | 10/1991 | Cobb, Jr. |
| 5,070,431 A | 12/1991 | Kitazawa et al. |
| 5,075,826 A | 12/1991 | Lan |
| 5,079,675 A | 1/1992 | Nakayama |
| 5,093,765 A | 3/1992 | Kashima et al. |
| 5,106,181 A | 4/1992 | Rockwell, III |
| 5,124,890 A | 6/1992 | Choi et al. |
| 5,134,549 A | 7/1992 | Yokoyama |
| 5,136,480 A | 8/1992 | Pristash et al. |
| 5,136,483 A | 8/1992 | Schoniger et al. |
| 5,150,965 A | 9/1992 | Fox |
| 5,165,187 A | 11/1992 | Shahidi-Hamedani et al. |
| 5,178,447 A | 1/1993 | Murase et al. |
| 5,207,493 A | 5/1993 | Murase et al. |
| 5,262,928 A | 11/1993 | Kashima et al. |
| 5,276,591 A | 1/1994 | Hegarty |
| 5,283,673 A | 2/1994 | Murase et al. |
| 5,303,322 A | 4/1994 | Winston et al. |
| 5,307,244 A | 4/1994 | Gaudette |
| 5,339,179 A | 8/1994 | Rudisill et al. |
| 5,349,503 A | 9/1994 | Blonder et al. |
| 5,375,043 A | 12/1994 | Tokunaga |
| 5,377,084 A | 12/1994 | Kojima et al. |
| 5,381,309 A | 1/1995 | Borchardt |
| 5,386,347 A | 1/1995 | Matsumoto |
| 5,390,085 A | 2/1995 | Mari-Roca et al. |
| 5,394,255 A | 2/1995 | Yokota et al. |
| 5,394,308 A | 2/1995 | Watanabe et al. |
| 5,396,350 A | 3/1995 | Beeson et al. |
| 5,414,947 A | 5/1995 | Hjaltason |
| 5,428,468 A | 6/1995 | Zimmerman et al. |
| 5,442,523 A | 8/1995 | Kashima et al. |
| 5,444,932 A | 8/1995 | Jeroma |
| 5,467,208 A | 11/1995 | Kokawa et al. |
| 5,467,417 A | 11/1995 | Nakamura et al. |
| 5,485,291 A | 1/1996 | Qiao et al. |
| 5,506,929 A | 4/1996 | Tai et al. |
| 5,521,342 A | 5/1996 | Barley et al. |
| 5,528,709 A | 6/1996 | Koike et al. |
| 5,536,558 A | 7/1996 | Shelton |
| 5,555,329 A | 9/1996 | Kuper et al. |
| 5,576,078 A | 11/1996 | Schatz |
| 5,579,134 A | 11/1996 | Lengyel |
| 5,584,556 A | 12/1996 | Yokoyama et al. |
| 5,590,945 A | 1/1997 | Simms |
| 5,598,281 A | 1/1997 | Zimmerman et al. |
| 5,600,462 A | 2/1997 | Suzuki et al. |
| 5,613,751 A | 3/1997 | Parker et al. |
| 5,618,095 A | 4/1997 | Kashima et al. |
| 5,649,754 A | 7/1997 | Matsumoto |
| 5,664,862 A | 9/1997 | Redmond et al. |
| 5,671,994 A | 9/1997 | Tai et al. |
| 5,711,592 A | 1/1998 | Hotta |
| 5,719,649 A | 2/1998 | Shono et al. |
| 5,771,328 A | 6/1998 | Wortman et al. |
| 5,775,791 A | 7/1998 | Yoshikawa et al. |
| 5,779,337 A | 7/1998 | Saito et al. |
| 5,779,338 A | 7/1998 | Ishikawa et al. |
| 5,808,784 A | 9/1998 | Ando et al. |
| 5,844,720 A | 12/1998 | Ohara et al. |
| 5,890,791 A | 4/1999 | Saito |
| 5,896,119 A | 4/1999 | Evanicky et al. |
| 5,917,664 A | 6/1999 | O'Neill et al. |
| 5,919,551 A | 7/1999 | Cobb, Jr. et al. |
| 5,931,555 A | 8/1999 | Akahane et al. |
| 5,961,198 A | 10/1999 | Hira et al. |
| 5,971,559 A | 10/1999 | Ishikawa et al. |
| 6,011,602 A | 1/2000 | Miyashita et al. |
| 6,036,329 A | 3/2000 | Iimura |
| 6,091,547 A | 7/2000 | Gardiner et al. |
| 6,120,280 A | 9/2000 | Mimura et al. |
| 6,130,730 A | 10/2000 | Jannson et al. |
| 6,151,169 A | 11/2000 | Kim |
| 6,167,182 A | 12/2000 | Shinohara et al. |
| 6,172,809 B1 | 1/2001 | Koike et al. |
| 6,712,481 B2 | 3/2004 | Parker et al. |
| 6,745,506 B2 | 6/2004 | Maas et al. |
| 6,752,505 B2 | 6/2004 | Parker et al. |
| 6,827,456 B2 | 12/2004 | Parker et al. |
| 6,966,684 B2 * | 11/2005 | Sommers et al. .............. 362/604 |
| 7,364,342 B2 | 4/2008 | Parker et al. |

FOREIGN PATENT DOCUMENTS

| | | |
|---|---|---|
| GB | 341968 | 1/1931 |
| JP | 08-271891 | 10/1996 |
| WO | WO 96/17207 | 6/1996 |
| WO | WO 96/27757 | 9/1996 |
| WO | WO 98/50806 | 11/1998 |
| WO | WO 99/42861 | 8/1999 |
| WO | WO 01/27527 | 4/2001 |

* cited by examiner

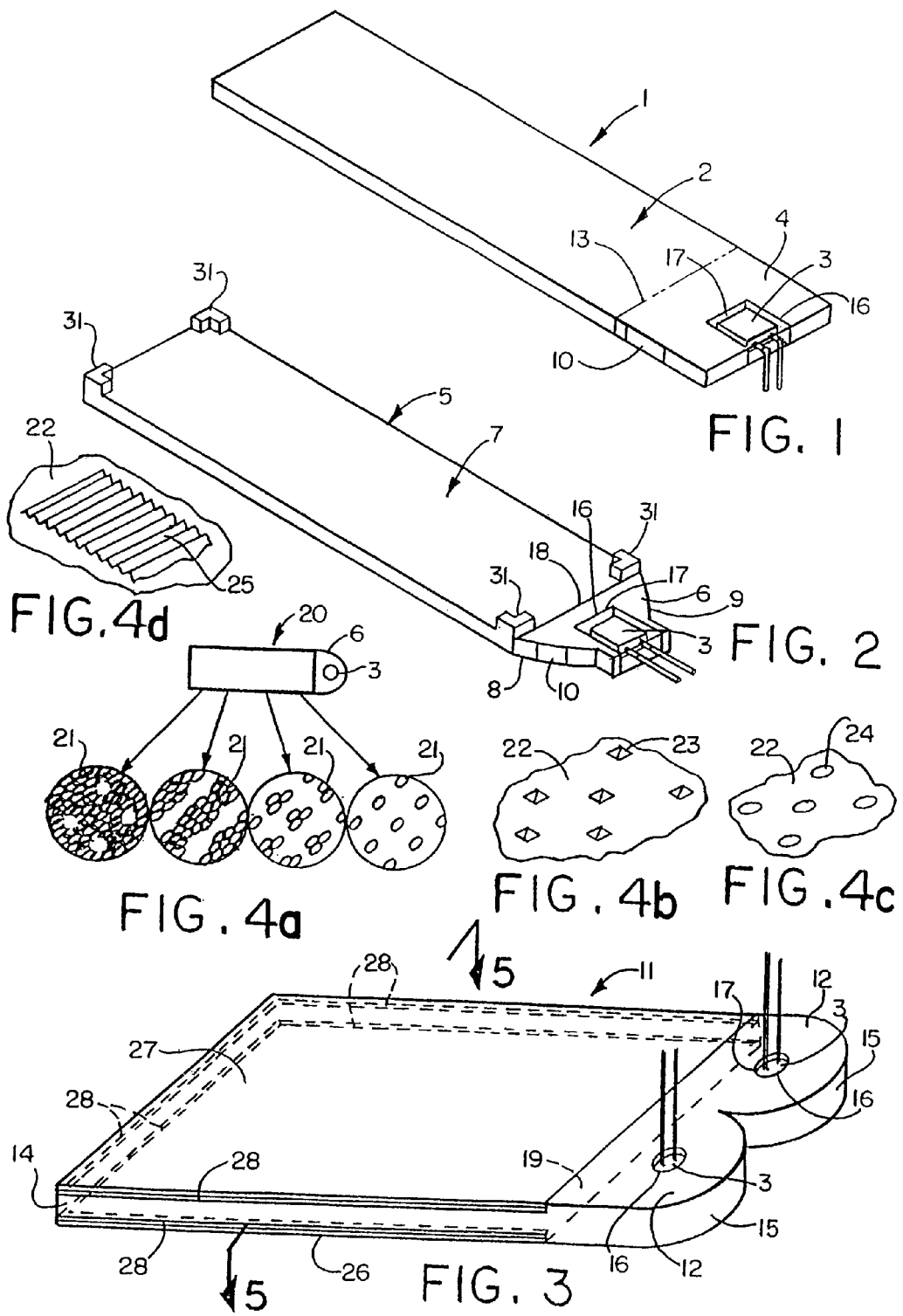

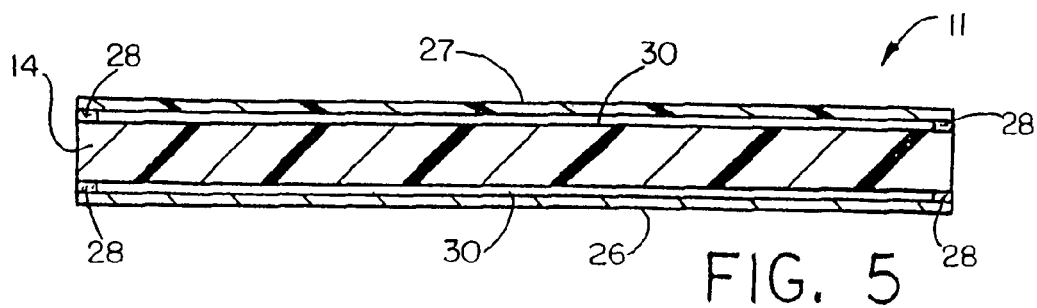
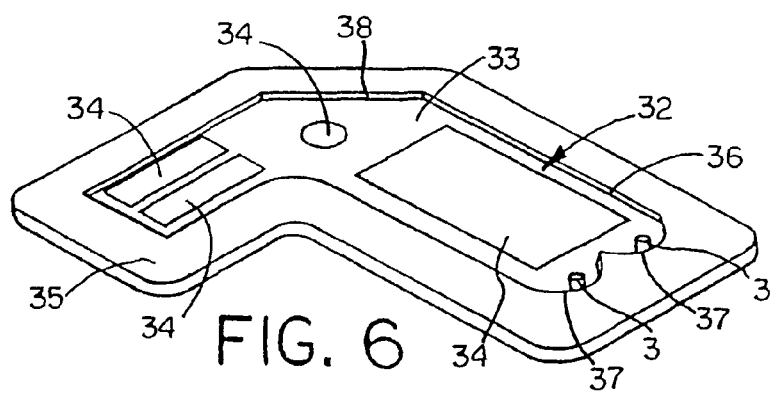
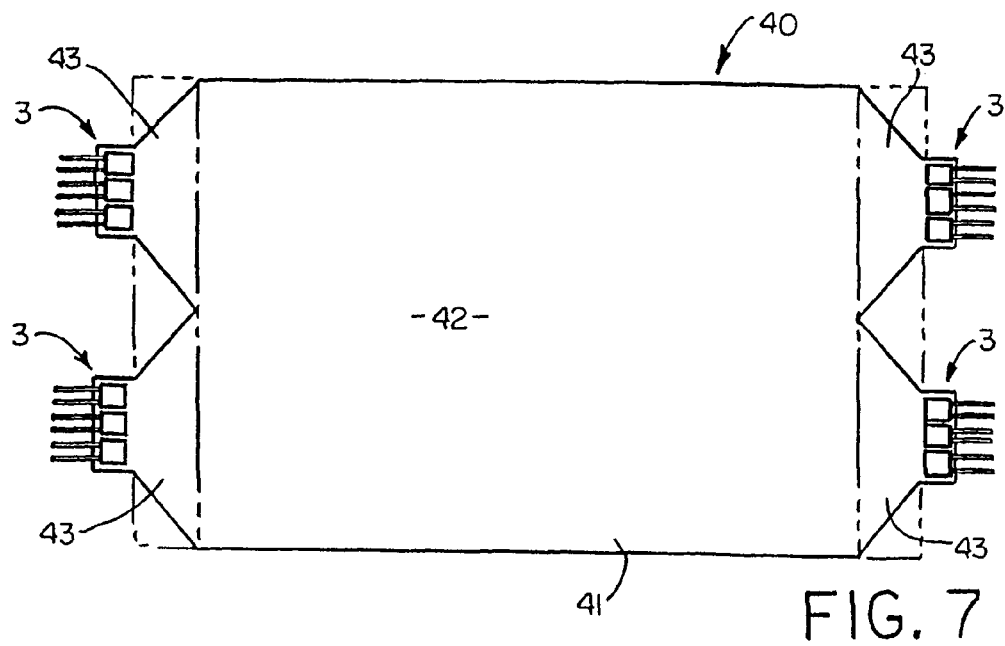
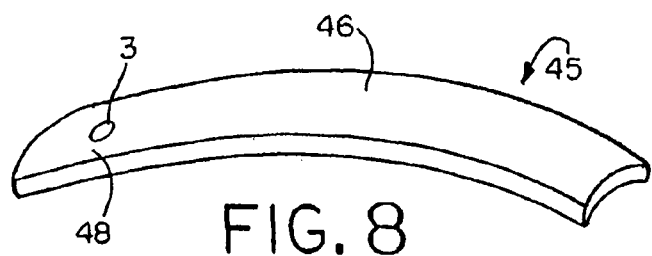

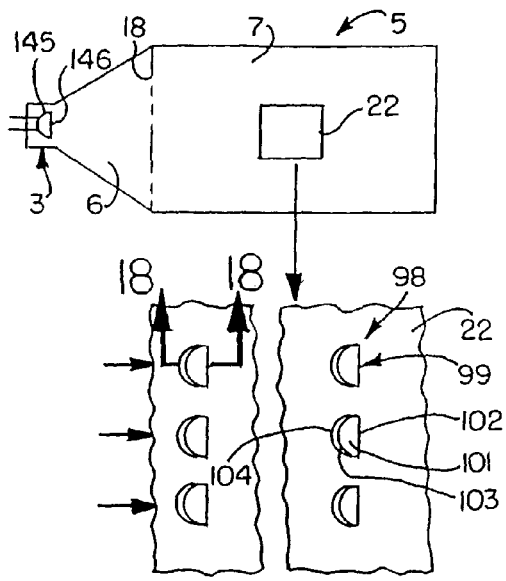
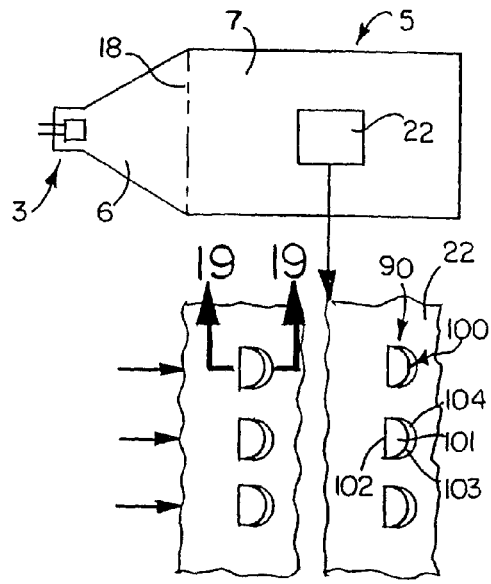
FIG. 16
FIG. 17
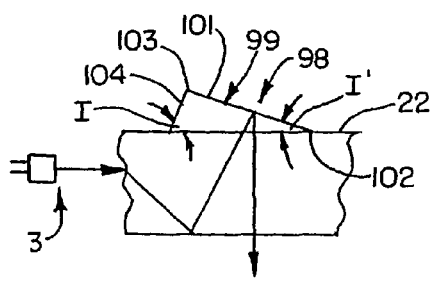
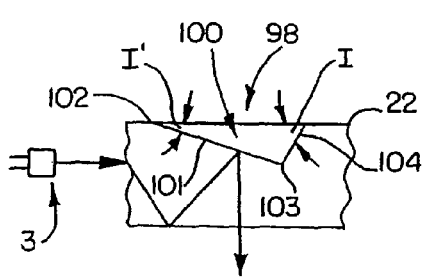
FIG. 18
FIG. 19
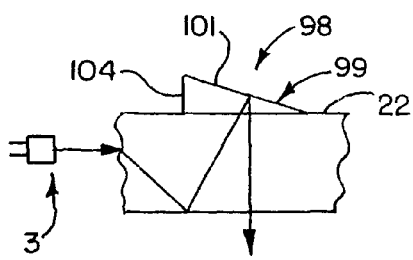
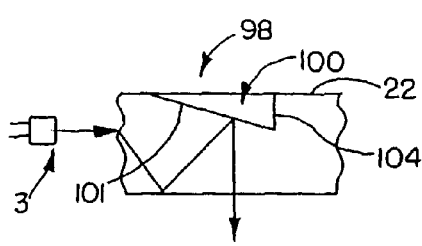
FIG. 20
FIG. 21

LIGHT EMITTING PANEL ASSEMBLIES

CROSS-REFERENCE TO RELATED APPLICATIONS

This application is a continuation of U.S. patent application Ser. No. 13/313,462, filed Dec. 7, 2011, which is a continuation of U.S. patent application Ser. No. 12/858,609, filed Aug. 18, 2010, now U.S. Pat. No. 8,104,944, dated Jan. 31, 2012, which is a continuation of U.S. patent application Ser. No. 12/429,226, filed Apr. 24, 2009, now U.S. Pat. No. 7,780,329, dated Aug. 24, 2010, which is a continuation of U.S. patent application Ser. No. 11/499,152, filed Aug. 4, 2006, now abandoned, which is a continuation of U.S. patent application Ser. No. 10/601,616, filed Jun. 23, 2003, now U.S. Pat. No. 7,108,414, dated Sep. 19, 2006, the entire disclosures of which are incorporated herein by reference.

BACKGROUND OF THE INVENTION

This invention relates generally, as indicated, to light emitting panel assemblies.

Light emitting panel assemblies are generally known. However, the present invention relates to several different light emitting panel assembly configurations which provide for better control of the light output from the panel assemblies and more efficient utilization of light to suit a particular application.

SUMMARY OF THE INVENTION

In accordance with one aspect of the invention, the light emitting panel assemblies include a light emitting panel member having a pattern of individual light extracting deformities of well defined shapes on or in one or more surface areas of the light emitting panel member.

In accordance with another aspect of the invention, the pattern of optical deformities may be varied in size, shape, density, placement, angle, rotation and/or type to obtain a desired light output distribution from the panel member to suit a particular application.

In accordance with another aspect of the invention, the pattern of optical deformities may be varied to obtain at least one light output distribution having a form or shape of at least one of text, graphics, logo or image.

In accordance with another aspect of the invention, the at least one light output distribution may be located in another light output distribution of the panel member to create a watermark or other effect in the another output distribution.

In accordance with another aspect of the invention, the optical deformities may be varied to obtain at least one multi-intensity light output distribution from the panel member to suit a particular application.

In accordance with another aspect of the invention, at least some of the optical deformities may be shaped or oriented preferentially to extract light propagating through the panel member in different directions.

In accordance with another aspect of the invention, at least some of the optical deformities may be shaped or oriented preferentially to cause different colored light propagating through the panel member in different directions to create at least one multi-colored light output distribution.

In accordance with another aspect of the invention, a plurality of panel members each having at least one different light output distribution may be disposed in overlying relation to one another to produce a composite light output distribution when viewed through the panel members or a display overlying the panel members.

In accordance with another aspect of the invention, the intensity of at least one light output distribution of each of the overlying panel members may be different to create a multi-intensity composite output distribution when viewed through the panel members.

In accordance with another aspect of the invention, at least one light redirecting film may be positioned over one or more overlying panel members to allow different light output distributions to be seen when the panel members are viewed through the film or a display overlying the film from different angles.

In accordance with another aspect of the invention, the pattern of optical deformities may be on or in one side of the panel member and additional optical deformities may be on or in the other side of the panel member to allow different output distributions to be seen when the panel member is viewed through the additional optical deformities in the other side.

These and other objects, advantages, features and aspects of the invention will become apparent as the following description proceeds.

To the accomplishment of the foregoing and related ends, the invention then comprises the features hereinafter fully described and particularly pointed out in the claims, the following description and the annexed drawings setting forth in detail certain illustrative embodiments of the invention, these being indicative, however, of but several of the various ways in which the principles of the invention may be employed.

BRIEF DESCRIPTION OF THE DRAWINGS

In the annexed drawings:

FIGS. 1 through 3 are schematic perspective views of three different forms of light emitting panel assemblies in accordance with this invention;

FIG. 4a is an enlarged plan view of a portion of a light output area of a panel assembly showing one form of pattern of light extracting deformities on the light output area;

FIGS. 4b, c and d are enlarged schematic perspective views of a portion of a light output area of a panel assembly showing other forms of light extracting deformities formed in or on the light output area;

FIG. 5 is an enlarged transverse section through the light emitting panel assembly of FIG. 3 taken generally on the plane of the line 5-5 thereof;

FIG. 6 is a schematic perspective view of another form of light emitting panel assembly in accordance with this invention;

FIG. 7 is a schematic top plan view of another form of light emitting panel assembly in accordance with this invention;

FIG. 8 is a schematic perspective view of another form of light emitting panel assembly in accordance with this invention;

FIGS. 16 and 17 are enlarged schematic fragmentary plan views of a surface area of a light panel assembly showing still other forms of light extracting deformities in accordance with this invention formed on or in a surface of the panel member;

FIGS. 18 and 19 are enlarged longitudinal sections through one of the light extracting deformities of FIGS. 16 and 17, respectively;

FIGS. 20 and 21 are enlarged schematic longitudinal sections through light extracting deformities similar to FIGS. 18 and 19, respectively, except that the deformity end walls are shown extending substantially perpendicular to the panel surface instead of perpendicular to their respective reflective/refractive surfaces as shown in FIGS. 18 and 19;

FIG. 44 is a schematic top plan view of another form of light emitting panel assembly in accordance with this invention for use in phototherapy treatment and the like;

FIGS. 45 through 47 are schematic side elevation views of still other forms of light emitting panel assemblies in accordance with this invention for use in phototherapy treatment and the like;

DETAILED DESCRIPTION OF THE INVENTION

Figure 9:
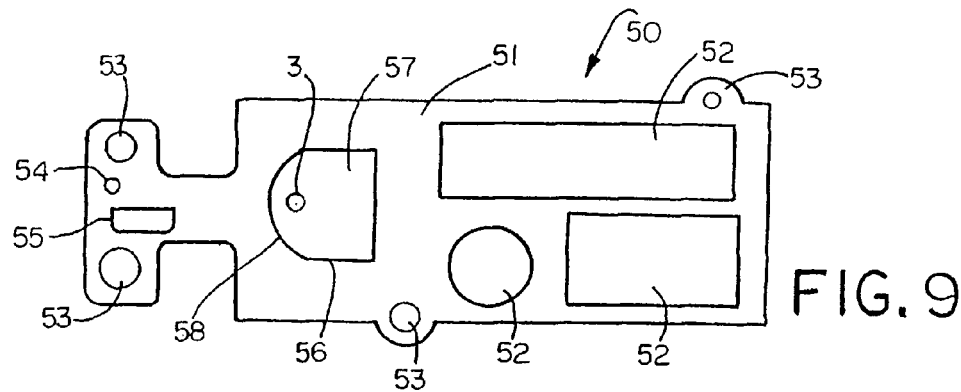
FIG. 9 is a schematic top plan view of another form of light emitting panel assembly in accordance with this invention.

Referring now in detail to the drawings, and initially to FIG. 1, there is schematically shown one form of light emitting panel assembly 1 in accordance with this invention including a transparent light emitting panel 2 and one or more light sources 3 which emit light in a predetermined pattern in a light transition member or area 4 used to make the transition from the light source 3 to the light emitting panel 2, as well known in the art. The light that is transmitted by the light transition area 4 to the transparent light emitting panel 2 may be emitted along the entire length of the panel or from one or more light output areas along the length of the panel as desired to produce a desired light output distribution to fit a particular application.

In FIG. 1 the light transition area 4 is shown as an integral extension of one end of the light emitting panel 2 and as being generally rectangular in shape. However, the light transition area may be of other shapes suitable for embedding, potting, bonding or otherwise mounting the light source. Also, reflective or refractive surfaces may be provided to increase efficiency. Moreover, the light transition area 4 may be a separate piece suitably attached to the light input surface 13 of the panel member if desired. Also, the sides of the light transition area may be curved to more efficiently reflect or refract a portion of the light emitted from the light source through the light emitting panel at an acceptable angle.

FIG. 2 shows another form of light emitting panel assembly 5 in accordance with this invention including a panel light transition area 6 at one end of the light emitting panel 7 with sides 8, 9 around and behind the light source 3 shaped to more efficiently reflect and/or refract and focus the light emitted from the light source 3 that impinges on these surfaces back through the light transition area 6 at an acceptable angle for entering the light input surface 18 at one end of the light emitting panel 7. Also, a suitable reflective material or coating 10 may be provided on the portions of the sides of the light transition areas of the panel assemblies of FIGS. 1 and 2 on which a portion of the light impinges for maximizing the amount of light or otherwise changing the light that is reflected back through the light transition areas and into the light emitting panels.

The panel assemblies shown in FIGS. 1 and 2 include a single light source 3, whereas FIG. 3 shows another light emitting panel assembly 11 in accordance with this invention including two light sources 3. Of course, it will be appreciated that the panel assemblies of the present invention may be provided with any number of light sources as desired, depending on the particular application.

The panel assembly 11 of FIG. 3 includes a light transition area 12 at one end of the light emitting panel 14 having reflective and/or refractive surfaces 15 around and behind each light source 3. These surfaces 15 may be appropriately shaped including for example curved, straight and/or faceted surfaces, and if desired, suitable reflective materials or coatings may be provided on portions of these surfaces to more efficiently reflect and/or refract and focus a portion of the light emitted for example from an incandescent light source which emits light in a 360° pattern through the light transition areas 12 into the light input surface 19 of the light emitting panel 14.

The light sources 3 may be mechanically held in any suitable manner in slots, cavities or openings 16 machined, molded or otherwise formed in the light transition areas of the panel assemblies. However, preferably the light sources 3 are embedded, potted or bonded in the light transition areas in order to eliminate any air gaps or air interface surfaces between the light sources and surrounding light transition areas, thereby reducing light loss and increasing the light output emitted by the light emitting panels. Such mounting of the light sources may be accomplished, for example, by bonding the light sources 3 in the slots, cavities or openings 16 in the light transition areas using a sufficient quantity of a suitable embedding, potting or bonding material 17. The slots, cavities or openings 16 may be on the top, bottom, sides or back of the light transition areas. Bonding can also be accomplished by a variety of methods that do not incorporate extra material, for example, thermal bonding, heat staking, ultrasonic or plastic welding or the like. Other methods of bonding include insert molding and casting around the light source(s).

A transparent light emitting material of any suitable type, for example acrylic or polycarbonate, may be used for the light emitting panels. Also, the panels may be substantially flat, or curved, may be a single layer or multi-layers, and may have different thicknesses and shapes. Moreover, the panels may be flexible, or rigid, and may be made out of a variety of compounds. Further, the panels may be hollow, filled with liquid, air, or be solid, and may have holes or ridges in the panels.

Each light source 3 may also be of any suitable type including, for example, any of the types disclosed in U.S. Pat. Nos. 4,897,771 and 5,005,108, assigned to the same assignee as the present application, the entire disclosures of which are incorporated herein by reference. In particular, the light sources 3 may be an arc lamp, an incandescent bulb which also may be colored, filtered or painted, a lens end bulb, a line light, a halogen lamp, a light emitting diode (LED), a chip from an LED, a neon bulb, a fluorescent tube, a fiber optic light pipe transmitting from a remote source, a laser or laser diode, or any other suitable light source. Additionally, the light sources 3 may be a multiple colored LED, or a combination of multiple colored radiation sources in order to provide a desired colored or white light output distribution. For example, a plurality of colored lights such as LEDs of different colors (red, blue, green) or a single LED with multiple colored chips may be flashed to create white light or any other desired colored light output distribution by varying the intensities of each different colored light or different colored chip.

A pattern of light extracting deformities or disruptions may be provided on one or both sides of the panel members or on one or more selected areas on one or both sides of the panel members, as desired. FIG. 4a schematically shows one such light surface area 20 on which a pattern of light extracting deformities or disruptions 21 is provided. As used herein, the term deformities or disruptions are used interchangeably to mean any change in the shape or geometry of the panel surface and/or coating or surface treatment that causes a portion of the light to be emitted. The pattern of light extracting deformities 21 shown in FIG. 4a includes a variable pattern which breaks up the light rays such that the internal angle of reflection of a portion of the light rays will be great enough to cause the light rays either to be emitted out of the panel through the side or sides on which the light extracting deformities 21 are provided or reflected back through the panel and emitted out the other side.

These deformities or disruptions 21 can be produced in a variety of manners, for example, by providing a painted pattern, an etched pattern, a machined pattern, a printed pattern, a hot stamped pattern, or a molded pattern or the like on selected light output areas of the panel members. An ink or printed pattern may be applied for example by pad printing, silk screening, ink jet, heat transfer film process or the like. The deformities may also be printed on a sheet or film which is used to apply the deformities to the panel member. This sheet or film may become a permanent part of the light panel assembly for example by attaching or otherwise positioning the sheet or film against one or both sides of the panel member similar to the sheet or film 27 shown in FIGS. 3 and 5 in order to produce a desired effect.

By varying the density, opaqueness or translucence, shape, depth, color, area, index of refraction, or type of deformities 21 on an area or areas of the panels, the light output of the panels can be controlled. The deformities or disruptions may be used to control the percent of light emitted from any area of the panels. For example, less and/or smaller size deformities 21 may be placed on panel areas where less light output is wanted. Conversely, a greater percentage of and/or larger deformities may be placed on areas of the panels where greater light output is desired.

Varying the percentages and/or size of deformities in different areas of the panel is necessary in order to provide a uniform light output distribution. For example, the amount of light traveling through the panels will ordinarily be greater in areas closer to the light source than in other areas further removed from the light source. A pattern of light extracting deformities 21 may be used to adjust for the light variances within the panel members, for example, by providing a denser concentration of light extracting deformities with increased distance from the light source 3 thereby resulting in a more uniform light output distribution from the light emitting panels.

The deformities 21 may also be used to control the output ray angle distribution of the emitted light to suit a particular application. For example, if the panel assemblies are used to provide a liquid crystal display back light, the light output will be more efficient if the deformities 21 cause the light rays to emit from the panels at predetermined ray angles such that they will pass through the liquid crystal display with low loss.

Additionally, the pattern of light extracting deformities may be used to adjust for light output variances attributed to light extractions of the panel members. The pattern of light extracting deformities 21 may be printed on the light output areas utilizing a wide spectrum of paints, inks, coatings, epoxies, or the like, ranging from glossy to opaque or both, and may employ half-tone separation techniques to vary the deformity 21 coverage. Moreover, the pattern of light extracting deformities 21 may be multiple layers or vary in index of refraction.

Print patterns of light extracting deformities 21 may vary in shapes such as dots, squares, diamonds, ellipses, stars, random shapes, and the like, and are desirably 0.006 square inch per deformity/element or less. Also, print patterns that are 60 lines per inch or finer are desirably employed, thus making the deformities or shapes 21 in the print patterns nearly invisible to the human eye in a particular application thereby eliminating the detection of gradient or banding lines that are common to light extracting patterns utilizing larger elements. Additionally, the deformities may vary in shape and/or size along the length and/or width of the panel members. Also, a random placement pattern of the deformities may be utilized throughout the length and/or width of the panel members. The deformities may have shapes or a pattern with no specific angles to reduce moiré or other interference effects. Examples of methods to create these random patterns are printing a pattern of shapes using stochastic print pattern techniques, frequency modulated half tone patterns, or random dot half tones. Moreover, the deformities may be colored in order to effect color correction in the panel members. The color of the deformities may also vary throughout the panel members, for example to provide different colors for the same or different light output areas.

In addition to or in lieu of the patterns of light extracting deformities 21 shown in FIG. 4a, other light extracting deformities including prismatic surfaces, depressions or raised surfaces of various shapes using more complex shapes in a mold pattern may be molded, etched, stamped, thermoformed, hot stamped or the like into or on one or more areas of the panel member. FIGS. 4b and 4c show panel areas 22 on which prismatic surfaces 23 or depressions 24 are formed in the panel areas, whereas FIG. 4d shows prismatic or other reflective or refractive surfaces 25 formed on the exterior of the panel area. The prismatic surfaces, depressions or raised surfaces will cause a portion of the light rays contacted thereby to be emitted from the panel member. Also, the angles of the prisms, depressions or other surfaces may be varied to direct the light in different directions to produce a desired light output distribution or effect. Moreover, the reflective or refractive surfaces may have shapes or a pattern with no specific angles to reduce moiré or other interference effects.

As best seen in the cross sectional view of FIG. 5, a back reflector (including trans reflectors) 26 may be attached or positioned against one side of the panel member 14 of FIG. 3 using a suitable adhesive 28 or other method in order to improve light output efficiency of the panel assembly 11 by reflecting the light emitted from that side back through the panel for emission through the opposite side. Additionally, a pattern of light extracting deformities 21, 23, 24 and/or 25 may be provided on one or both sides of the panel member in order to change the path of the light so that the internal critical angle is exceeded and a portion of the light is emitted from one or both sides of the panel. Moreover, a transparent film, sheet or plate 27 may be attached or positioned against the side or sides of the panel member from which light is emitted using a suitable adhesive 28 or other method in order to produce a desired effect.

The member 27 may be used to further improve the uniformity of the light output distribution. For example, the member 27 may be a colored film, a diffuser, or a label or display, a portion of which may be a transparent overlay that may be colored and/or have text or an image thereon.

If adhesive 28 is used to adhere the back reflector 26 and/or film 27 to the panel, the adhesive is preferably applied only along the side edges of the panel, and if desired the end edge opposite the light transition areas 12, but not over the entire surface area or areas of the panel because of the difficulty in consistently applying a uniform coating of adhesive to the panel. Also, the adhesive changes the internal critical angle of the light in a less controllable manner than the air gaps 30 (see FIG. 5) which are formed between the respective panel surfaces and the back reflector 26 and/or film 27 when only adhered along the peripheral edges. Additionally, longer panel members are achievable when air gaps 30 are used. If adhesive were to be used over the entire surface, the pattern of deformities could be adjusted to account for the additional attenuation in the light caused by the adhesive.

Referring further to FIG. 2, the panel assembly 5 shown therein also includes molded posts 31 at one or more corners of the panel 7 (four such posts being shown) which may be used to facilitate mounting of the panel assembly and providing structural support for other parts or components, for example, a display panel such as a liquid crystal display panel as desired.

FIG. 6 shows another form of light emitting panel assembly 32 in accordance with this invention including a panel member 33, one or more light sources 3, and one or more light output areas 34. In addition, the panel assembly 32 includes a tray 35 having a cavity or recess 36 in which the panel assembly 32 is received. The tray 35 may act as a back reflector as well as end edge and/or side edge reflectors for the panel 33 and side and/or back reflectors 37 for the light sources 3. Additionally, one or more secondary reflective or refractive surfaces 38 may be provided on the panel member 33 and/or tray 35 to reflect a portion of the light around one or more corners or curves in a non-rectangular shaped panel member 33. These secondary reflective/refractive surfaces 38 may be flat, angled, faceted or curved, and may be used to extract a portion of the light away from the panel member in a predetermined pattern. FIG. 6 also shows multiple light output areas 34 on the panel member that emit light from one or more light sources 3.

FIG. 7 is a schematic illustration of still another form of light emitting panel assembly 40 in accordance with this invention including a panel member 41 having one or more light output areas 42 and one or more light transition areas (mixing areas) 43 containing a plurality of light sources 3 at one or both ends of the panel. Each transition area mixes the light from one or more light sources having different colors and/or intensities. In this particular embodiment, each of the light sources 3 desirably employs three colored LEDs (red, blue, green) in each transition mixing area 43 so that the light from the three LEDs can be mixed to produce a desired light output color that will be emitted from the light output area 42. Alternatively, each light source may be a single LED having multiple colored chips bonded to the lead film. Also, two colored LEDs or a single LED having two colored chips may be used for a particular application. By varying the intensities of the individual respective LEDs, virtually any colored light output or white light distribution can be achieved.

FIG. 8 shows yet another form of light emitting panel assembly 45 in accordance with this invention including a light emitting panel member 46 and a light source 3 in a light transition area 48 integral with one end of the panel member. In this particular embodiment, the panel member 46 is three-dimensionally curved, for example, such that light rays may be emitted in a manner that facilitates aesthetic design of a lighted display.

FIG. 9 schematically shows another form of light emitting panel assembly 50 in accordance with this invention, including a panel member 51 having multiple light output areas 52, and mounting posts and/or mounting tabs 53. This particular panel assembly 50 may serve as a structural member to support other parts or components as by providing holes or cavities 54, 55 in the panel member 51 which allow for the insertion of modular components or other parts into the panel member. Moreover, a separate cavity or recess 56 may be provided in the panel member 51 for receipt of a correspondingly shaped light transition area 57 having one or more light sources 3 embedded, bonded, cast, insert molded, epoxied, or otherwise mounted or positioned therein and a curved reflective or refractive surface 58 on the transition area 57 and/or wall of the cavity or recess 56 to redirect a portion of the light in a predetermined manner. In this way the light transition area 57 and/or panel member may be in the form of a separate insert which facilitates the easy placement of the light source in a modular manner. A reflector 58 may be placed on the reflective or refractive surface of the cavity or recess 56 or insert 57. Where the reflector 58 is placed on the reflective or refractive surface of the cavity or recess 56, the cavity or recess may act as a mold permitting transparent material from which the transition area 57 is made to be cast around one or more light sources 3.

Figure 10:
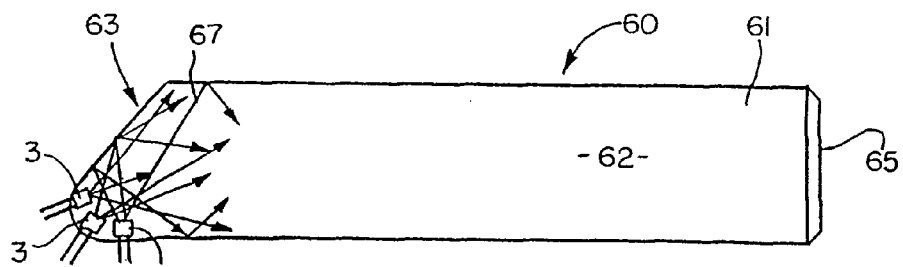
FIG. 10 is a schematic top plan view of still another form of light emitting panel assembly in accordance with this invention.
Figure 11:
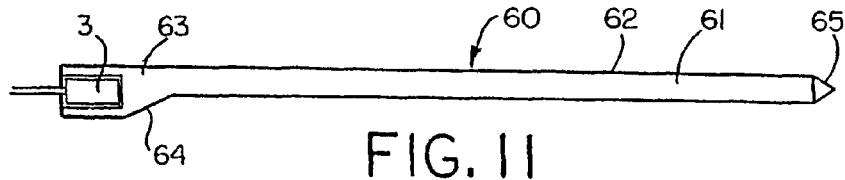
FIG. 11 is a side elevation view of the light emitting panel assembly of FIG. 10.
Figure 11A:
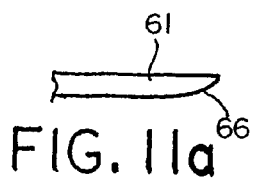
FIG. 11a is a fragmentary side elevation view showing a tapered or rounded end on the panel member in place of the prismatic surface shown in FIGS. 10 and 11.

FIGS. 10 and 11 schematically show another form of light emitting panel assembly 60 in accordance with this invention including a panel member 61 having one or more light output areas 62. In this particular embodiment, an off-axis light transition area 63 is provided that is thicker in cross section than the panel member to permit use of one or more light sources 3 embedded or otherwise mounted in the light transition area that are dimensionally thicker than the panel member. Also, a three-dimensional reflective surface 64 (FIG. 11) may be provided on the transition area 63. Moreover, a prism 65 (FIG. 11) or tapered, rounded, or otherwise shaped end 66 (FIG. 11a) may be provided at the end of the panel opposite the light sources 3 to perform the function of an end reflector. The light sources 3 may be oriented at different angles relative to each other and offset to facilitate better mixing of the light rays 67 in the transition area 63 as schematically shown in FIG. 10 and/or to permit a shorter length transition area 63 to be used.

Figure 12:
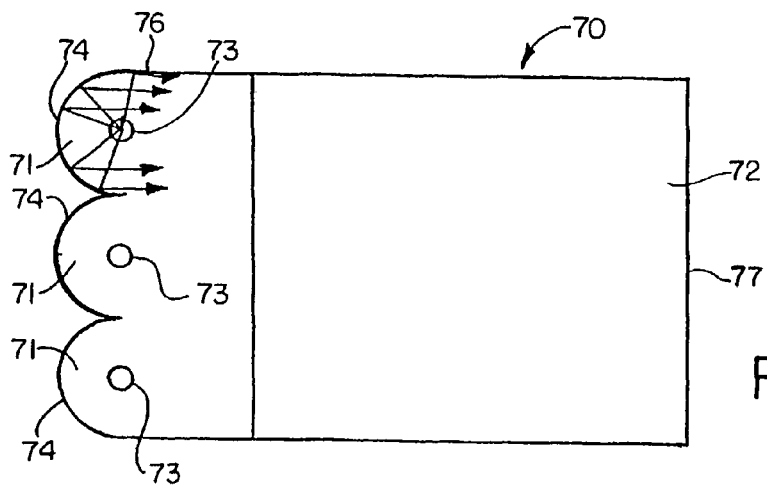
FIG. 12 is a schematic top plan view of another form of light emitting panel assembly in accordance with this invention.
Figure 13:
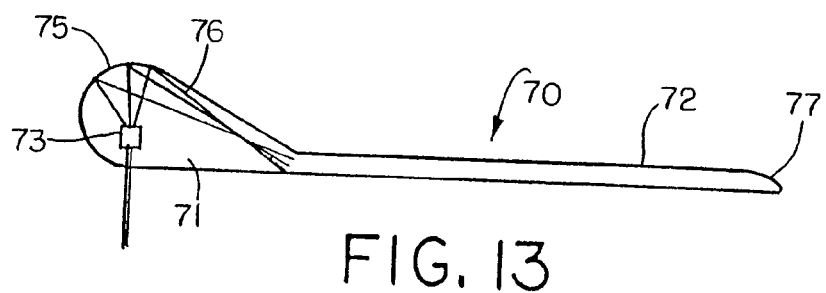
FIG. 13 is a schematic side elevation view of the light emitting panel assembly of FIG. 12.

FIGS. 12 and 13 schematically show still another form of light emitting panel assembly 70 in accordance with this invention which includes one or more light transition areas 71 at one or both ends of the panel member 72 each containing a single light source 73. The transition area or areas 71 shown in FIGS. 12 and 13 collect light with multiple or three-dimensional surfaces and/or collect light in more than one plane. For example each transition area 71 shown in FIGS. 12 and 13 has elliptical and parabolic shape surfaces 74 and 75 in different planes for directing the light rays 76 into the panel member at a desired angle.

Providing one or more transition areas at one or both ends of the panel member of any desired dimension to accommodate one or more light sources, with reflective and/or refractive surfaces on the transition areas for redirecting the light rays into the panel member at relatively low angles allows the light emitting panel member to be made much longer and thinner than would otherwise be possible. For example the panel members of the present invention may be made very thin, i.e., 0.125 inch thick or less.

Figure 14:
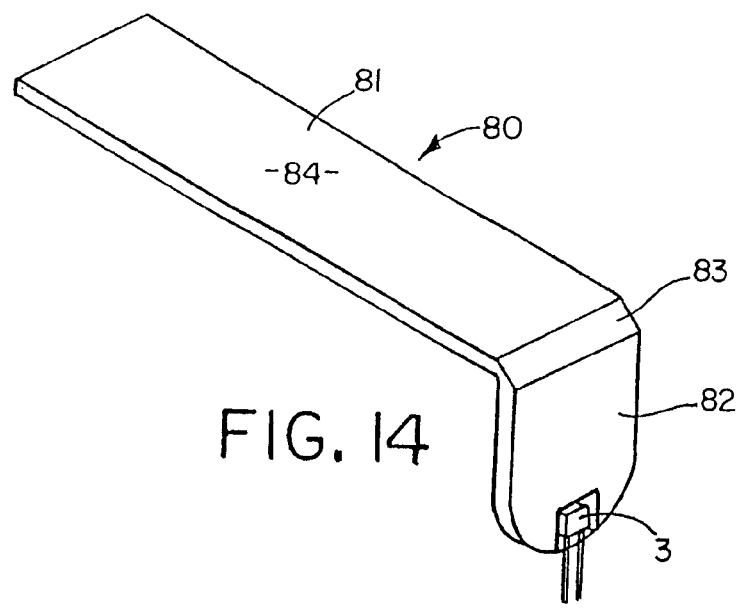
FIGS. 14 and 15 are schematic perspective views of still other forms of light emitting panel assemblies in accordance with this invention.

FIG. 14 schematically illustrates still another form of light emitting panel assembly 80 in accordance with this invention including a light emitting panel 81 and one or more light sources 3 positioned, embedded, potted, bonded or otherwise mounted in a light transition area 82 that is at an angle relative to the panel member 81 to permit more efficient use of space. An angled or curved reflective or refractive surface 83 is provided at the junction of the panel member 81 with the transition area 82 in order to reflect/refract light from the light source 3 into the body of the panel member 81 for emission of light from one or more light emitting areas 84 along the length of the panel member.

Figure 15:
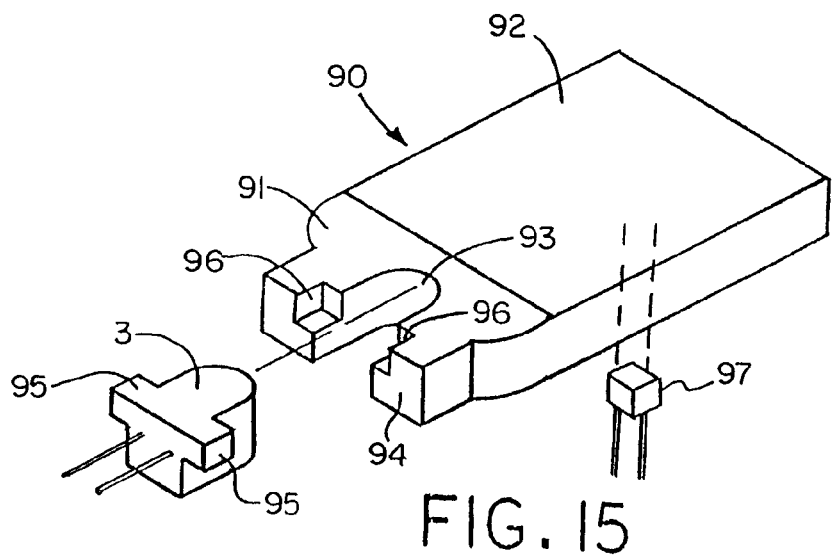

FIG. 15 schematically illustrates still another form of light emitting panel assembly 90 in accordance with this invention including a light transition area 91 at one or both ends of a light emitting panel member 92 containing a slot 93 for sliding receipt of an LED or other suitable light source 3. Preferably the slot 93 extends into the transition area 91 from the back edge 94, whereby the light source 3 may be slid and/or snapped in place in the slot from the back, thus allowing the transition area to be made shorter and/or thinner. The light source 3 may be provided with wings, tabs or other surfaces 95 for engagement in correspondingly shaped recesses or grooves 96 or the like in the transition area 91 for locating and, if desired, securing the light source in place. Also, the light source 3 may be embedded, potted, bonded or otherwise secured within the slot 93 in the light transition area 91 of the panel member 92. Light from a secondary light source 97 may be projected through the panel member 92 for indication or some other effect.

FIG. 16 through 19 show other light extracting deformities 98 in accordance with this invention which may either be individual projections 99 on the respective panel surface areas 22 or individual depressions 100 in such panel surface areas. In either case, the light extracting deformities 98 differ from the light extracting deformities shown in FIGS. 4a, 4b, 4c and 4d in that each of the deformities 98 has a well defined shape including a reflective or refractive surface 101 that intersects the respective panel surface area 22 at one edge 102 and has a uniform slope throughout its length for more precisely controlling the emission of light by each of the deformities. Along a peripheral edge portion 103 of each reflective/refractive surface 101 is an end wall 104 of each deformity 98 that intersects the respective panel surface area at a greater included angle I than the included angle I' between the reflective/refractive surfaces 101 and the panel surface area 22 (see FIGS. 18 and 19) to minimize the projected surface area of the end walls on the panel surface area. This allows more deformities 98 to be placed on or in the panel surface areas than would otherwise be possible if the projected surface areas of the end walls 104 were substantially the same as or greater than the projected surface areas of the reflective/refractive surfaces 101.

In FIGS. 16 and 17 the peripheral edge portions 103 of the reflective/refractive surfaces 101 and associated end walls 104 are curved in the transverse direction. Also, in FIGS. 18 and 19 the end walls 104 of the deformities 98 are shown extending substantially perpendicular to the reflective/refractive surfaces 101 of the deformities. Alternatively, such end walls 104 may extend substantially perpendicular to the panel surface areas 22 as schematically shown in FIGS. 20 and 21. This virtually eliminates any projected surface area of the end walls 104 on the panel surface areas 22 whereby the density of the deformities on the panel surface areas may be even further increased.

Figure 22:
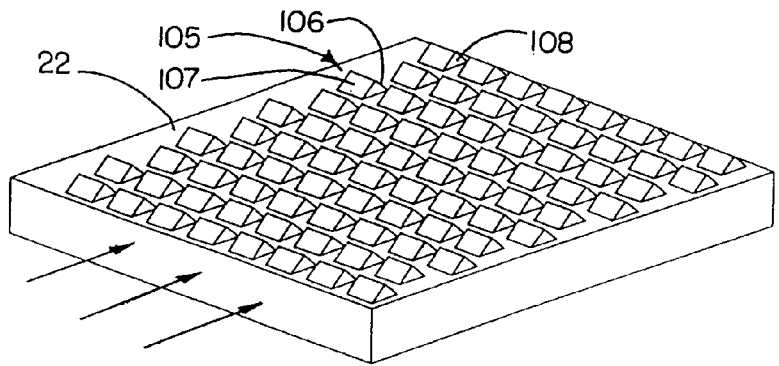
FIGS. 22 through 30 are enlarged schematic perspective views of panel surface areas containing various patterns of individual light extracting deformities of other well defined shapes in accordance with this invention.
Figure 23:
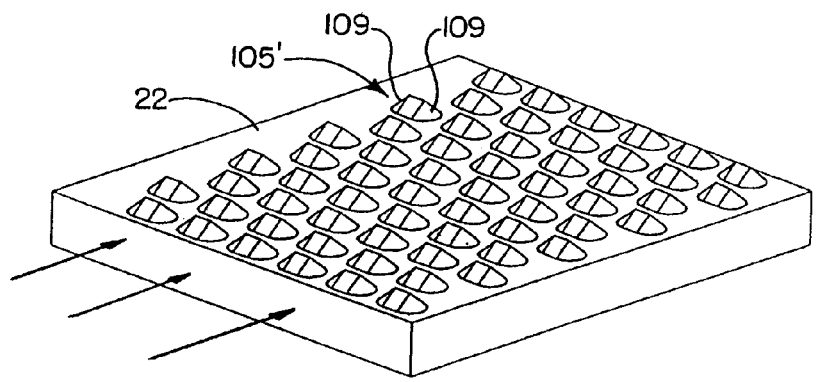

The light extracting deformities may also be of other well defined shapes to obtain a desired light output distribution from a panel surface area. FIG. 22 shows individual light extracting deformities 105 on a panel surface area 22 each including a generally planar, rectangular reflective/refractive surface 106 and associated end wall 107 of a uniform slope throughout their length and width and generally planar side walls 108. Alternatively, the deformities 105' may have rounded or curved side walls 109 as schematically shown in FIG. 23.

Figure 24:
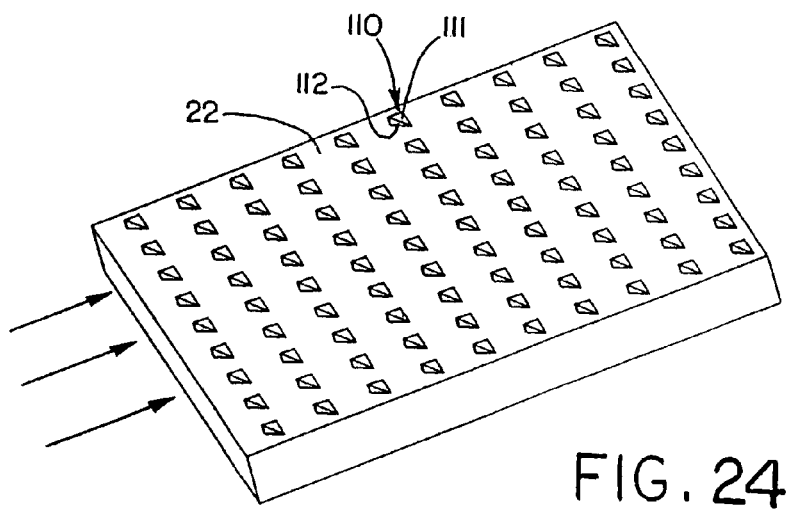
Figure 25:
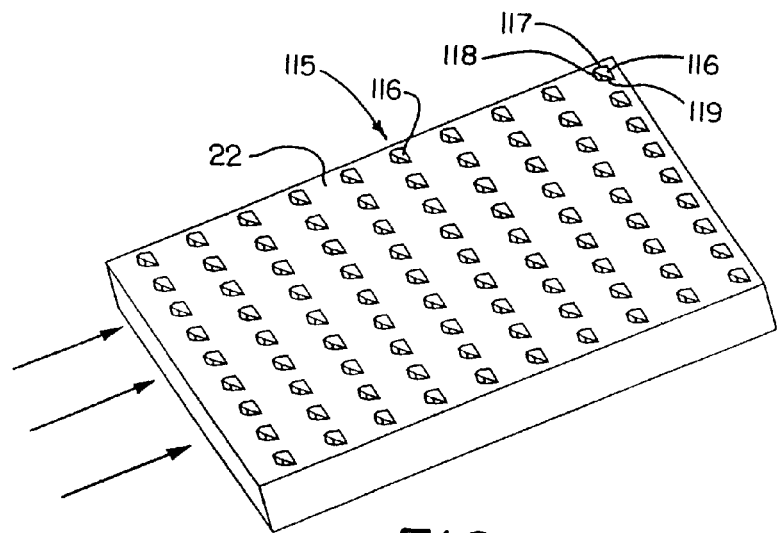

FIG. 24 shows individual light extracting deformities 110 on a panel surface area 22 each including a planar, sloping triangular shaped reflective/refractive surface 111 and associated planar, generally triangularly shaped side walls or end walls 112. FIG. 25 shows individual light extracting deformities 115 each including a planar sloping reflective/refractive surface 116 having angled peripheral edge portions 117 and associated angled end and side walls 118 and 119.

Figure 26:
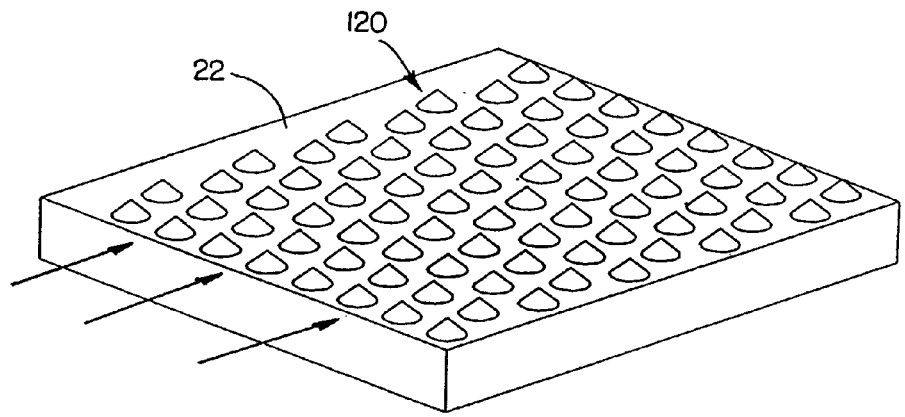
Figure 27:
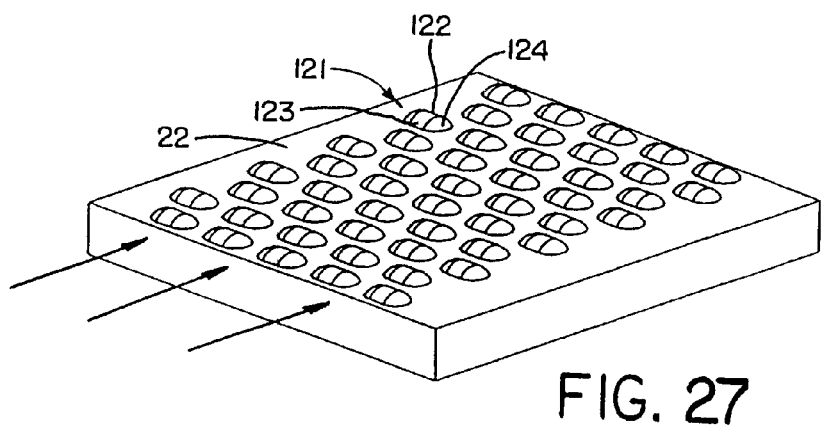

FIG. 26 shows individual light extracting deformities 120 which are generally conically shaped, whereas FIG. 27 shows individual light extracting deformities 121 each including a rounded reflective/refractive surface 122 and rounded end wall 123 and rounded or curved side walls 124 all blended together.

Figure 28:
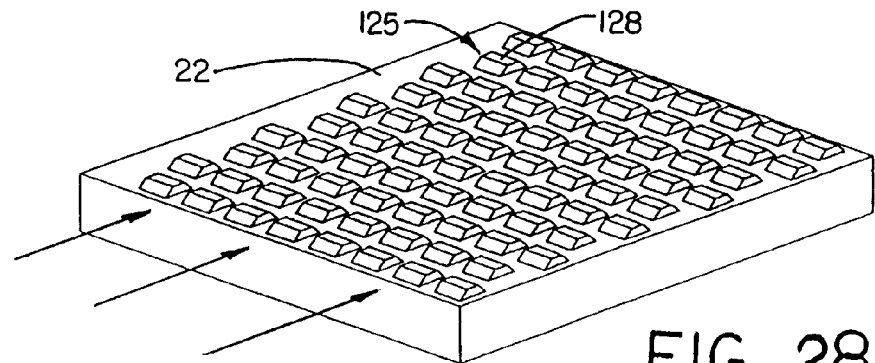
Figure 29:
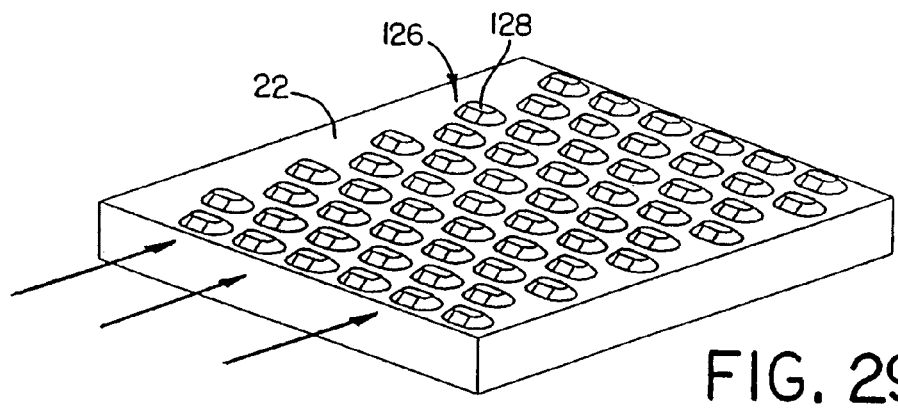
Figure 30:
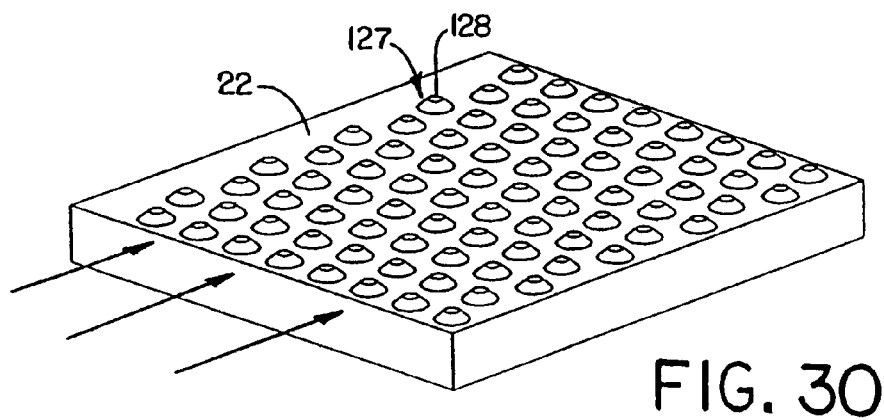
Figure 31:
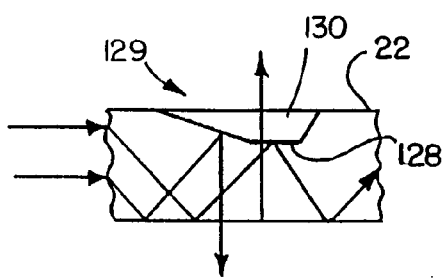
FIG. 31 is an enlarged schematic longitudinal section through another form of light extracting deformity in accordance with this invention.

Regardless of the particular shape of the reflective/refractive surfaces and end and side walls of the individual deformities, such deformities may also include planar surfaces intersecting the reflective/refractive surfaces and end and/or side walls in parallel spaced relation to the panel surface areas 22. FIGS. 28 through 30 show deformities 125, 126 and 127 in the form of individual projections on a panel surface area 22 having representative shapes similar to those shown in FIGS. 22, 23 and 26, respectively, except that each deformity is intersected by a planar surface 128 in parallel spaced relation to the panel surface area 22. In like manner, FIG. 31 shows one of a multitude of deformities 129 in the form of individual depressions 130 in a panel surface area 22 each intersected by a planar surface 128 in parallel spaced relation to the general planar surface of the panel surface area 22. Any light rays that impinge on such planar surfaces 128 at internal angles less than the critical angle for emission of light from the panel surface area 22 will be internally reflected by the planar surfaces 128, whereas any light rays impinging on such planar surfaces 128 at internal angles greater than the critical angle will be emitted by the planar surfaces with minimal optical discontinuities as schematically shown in FIG. 31.

Where the deformities are projections on the panel surface area 22, the reflective/refractive surfaces extend at an angle away from the panel in a direction generally opposite to that in which the light rays from the light source 3 travel through the panel as schematically shown in FIGS. 18 and 20. Where the deformities are depressions in the panel surface area, the reflective/refractive surfaces extend at an angle into the panel in the same general direction in which the light rays from the light source 3 travel through the panel member as schematically shown in FIGS. 19 and 21.

Regardless of whether the deformities are projections or depressions on or in the panel surface areas 22, the slopes of the light reflecting/refractive surfaces of the deformities may be varied to cause the light rays impinging thereon to be either refracted out of the light emitting panel or reflected back through the panel and emitted out the opposite side of the panel which may be etched to diffuse the light emitted therefrom or covered by a transparent film, sheet or plate similar to the film 27 shown in FIGS. 3 and 5 to produce a desired effect.

Figure 32:
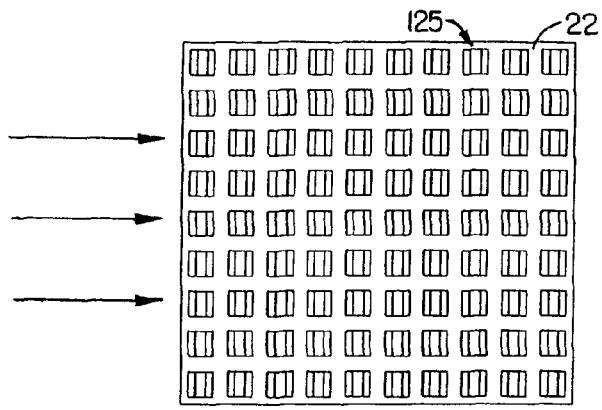
FIGS. 32 and 33 are enlarged schematic top plan views of panel surface areas containing light extracting deformities similar in shape to those shown in FIGS. 28 and 29 arranged in a plurality of straight rows along the length and width of the panel surface area.
Figure 33:
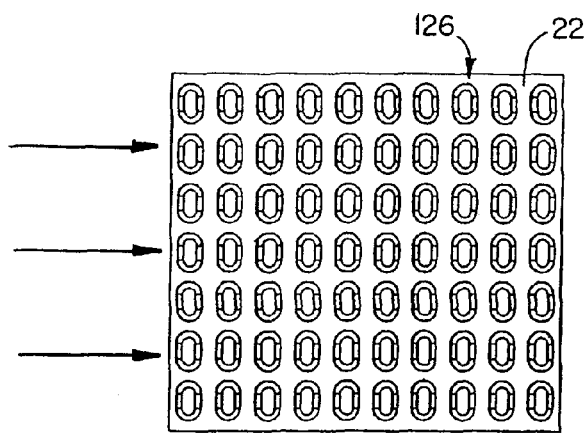
Figure 34:
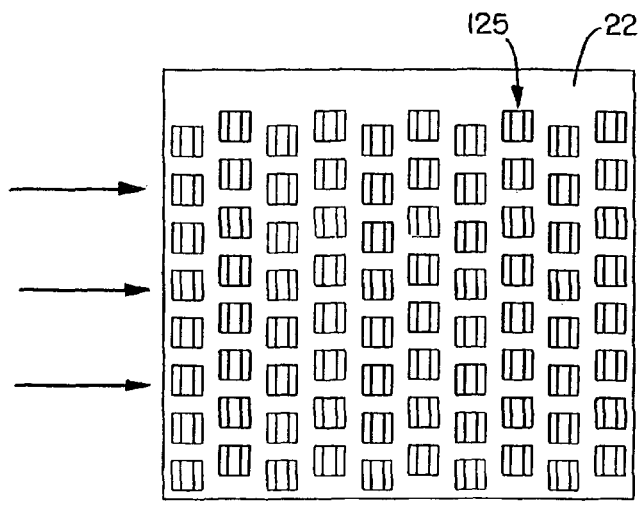
FIGS. 34 and 35 are enlarged schematic top plan views of panel surface areas containing light extracting deformities also similar in shape to those shown in FIGS. 28 and 29 arranged in staggered rows along the length of the panel surface areas.
Figure 35:
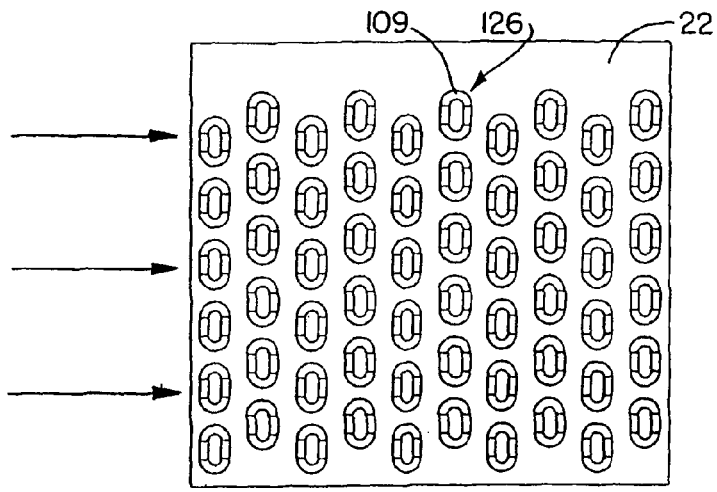

Also, the pattern of light extracting deformities on the panel surface areas may be uniform or variable as desired to obtain a desired light output distribution from the panel surface areas. FIGS. 32 and 33 show deformities 125 and 126 similar in shape to those shown in FIGS. 28 and 29 arranged in a plurality of generally straight uniformly spaced apart rows along the length and width of a panel surface area 22, whereas FIGS. 34 and 35 show such deformities 125 and 126 arranged in staggered rows along the length of a panel surface area.

Figure 36:
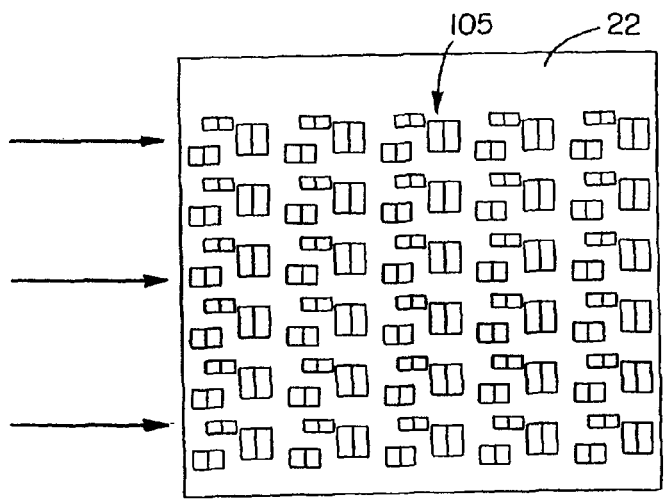
FIGS. 36 and 37 are enlarged schematic top plan views of panel surface areas containing a random or variable pattern of different sized light emitting deformities on the panel surface areas.
Figure 37:
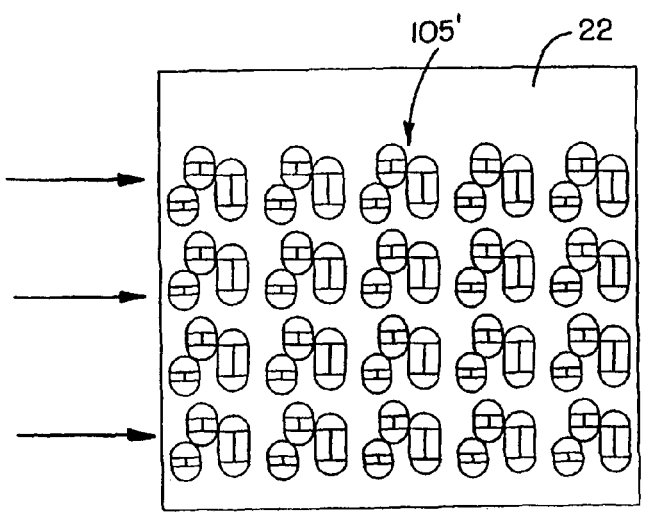
Figure 38:
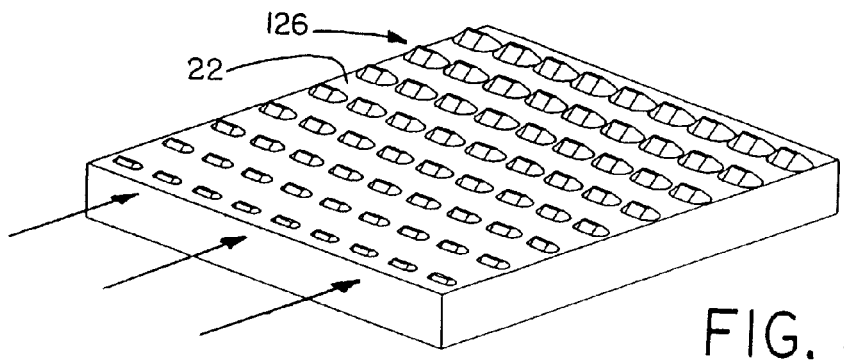
FIG. 38 is an enlarged schematic perspective view of a panel surface area showing light extracting deformities in accordance with this invention increasing in size as the distance of the deformities from the light source increases or intensity of the light increases along the length of the panel surface area.

Also, the size, including the width, length and depth or height as well as the angular orientation and position or location of the light extracting deformities may vary along the length and/or width of any given panel surface area to obtain a desired light output distribution from the panel surface area. FIGS. 36 and 37 show a random or variable pattern of different sized deformities 105 and 105' similar in shape to those shown in FIGS. 22 and 23, respectively, arranged in staggered rows on a panel surface area 22, whereas FIG. 38 shows deformities 126 similar in shape to those shown in FIG. 29 increasing in size as the distance of the deformities from the light source increases or intensity of the light decreases along the length and/or width of the panel surface area 22.

Figure 39:
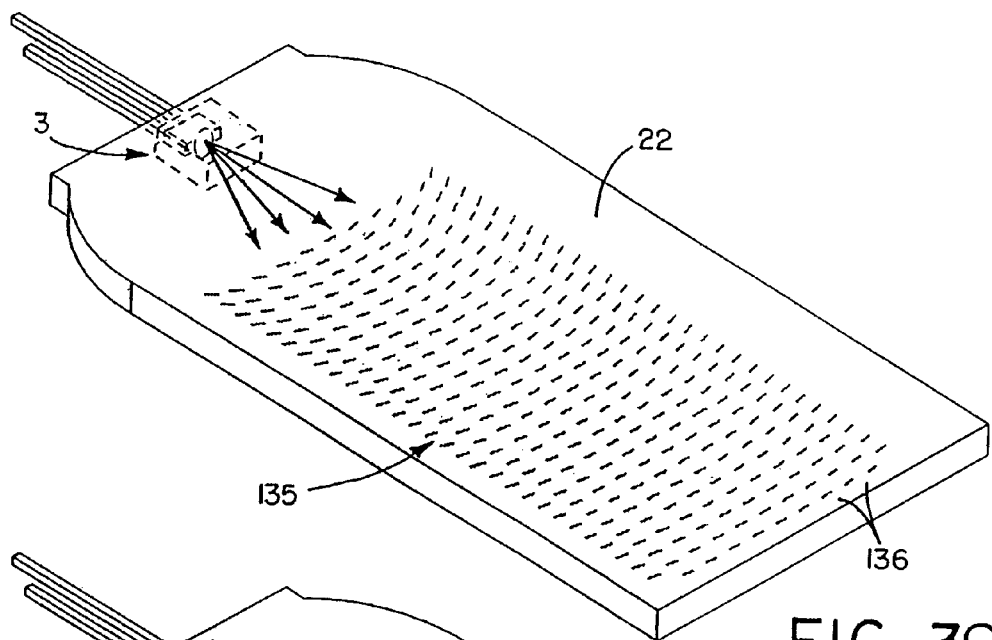
FIGS. 39 and 40 are schematic perspective views showing different angular orientations of the light extracting deformities along the length and width of a panel surface area.
Figure 40:
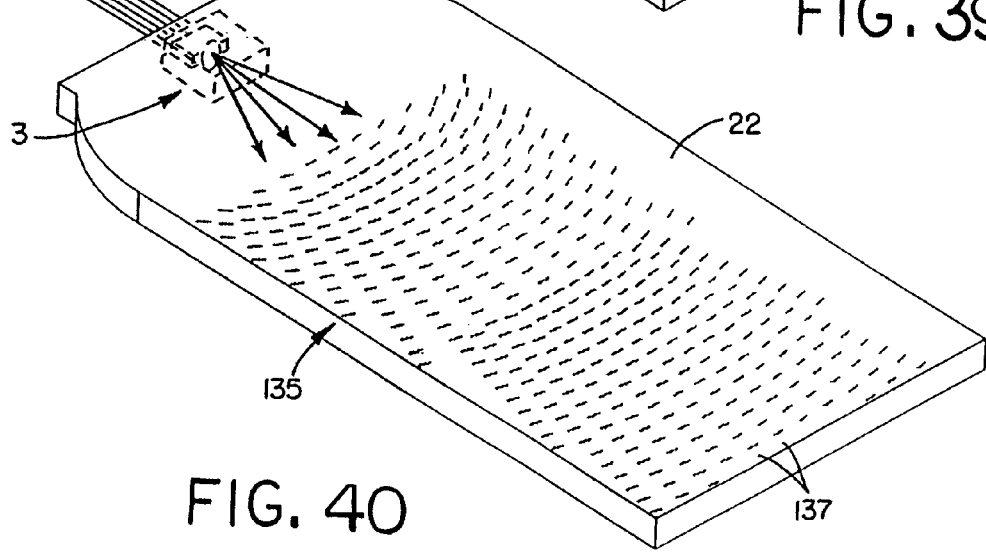

FIGS. 39 and 40 schematically show different angular orientations of light extracting deformities 135 of any desired shape along the length and width of a panel surface area 22. In FIG. 39 the light extracting deformities 135 are arranged in straight rows 136 along the length of the panel surface area but the deformities in each of the rows are oriented to face the light source 3 so that all of the deformities are substantially in line with the light rays being emitted from the light source. In FIG. 40 the deformities 135 are also oriented to face the light source 3 similar to FIG. 39. In addition, the rows 137 of deformities in FIG. 40 are in substantial radial alignment with the light source.

Figure 41:
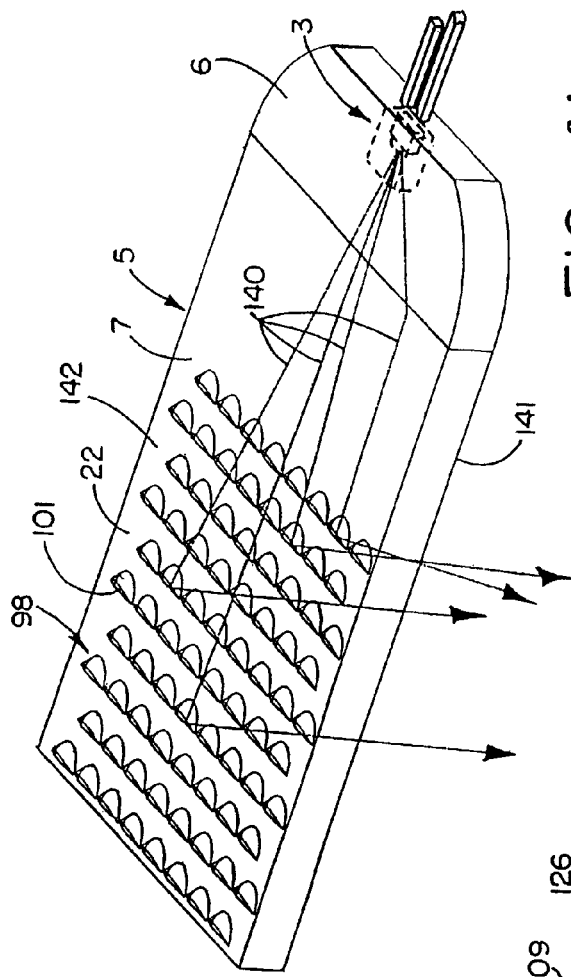
FIGS. 41 and 42 are enlarged perspective views schematically showing how exemplary light rays emitted from a focused light source are reflected or refracted by different individual light extracting deformities of well defined shapes in accordance with this invention.
Figure 42:
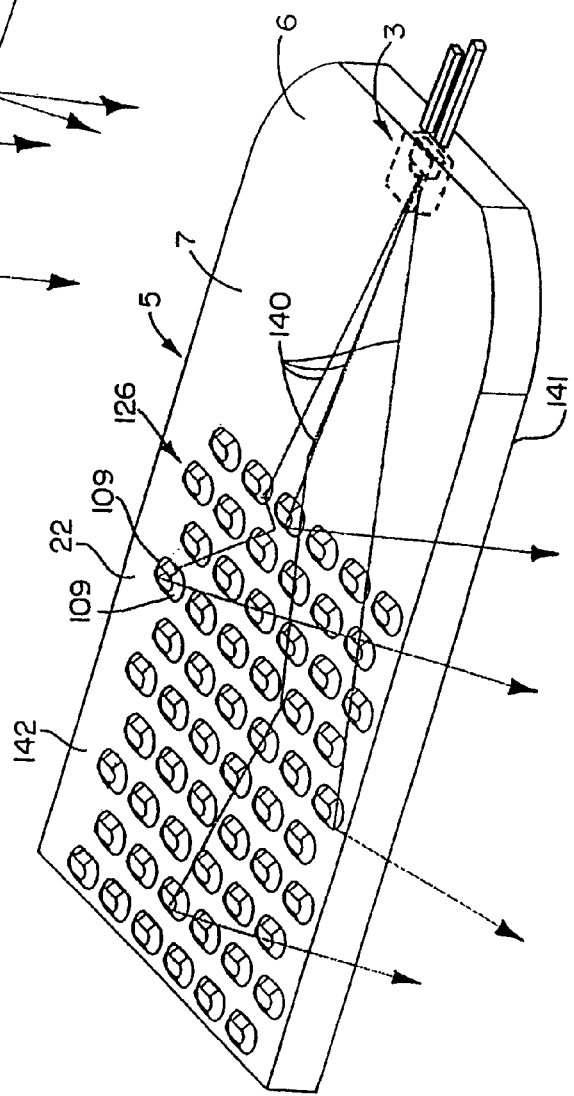

FIGS. 41 and 42 schematically show how exemplary light rays 140 emitted from a focused light source 3 insert molded or cast within a light transition area 6 of a light emitting panel assembly 5 in accordance with this invention are reflected during their travel through the light emitting panel member 7 until they impinge upon individual light extracting deformities 98, 126 of well defined shapes on or in a panel surface area 22 causing more of the light rays to be reflected or refracted out of one side 141 of the panel member than the other side 142. In FIG. 41 the exemplary light rays 140 are shown being reflected by the reflective/refractive surfaces 101 of the deformities 98 in the same general direction out through the same side 141 of the panel member, whereas in FIG. 42 the light rays 140 are shown being scattered in different directions within the panel member 7 by the rounded side walls 109 of the deformities 126 before the light rays are reflected/refracted out of the same side 141 of the panel member. Such a pattern of individual light extracting deformities of well defined shapes in accordance with the present invention can cause 60 to 70% or more of the light received through the input edge 18 of the panel member to be emitted from the same side of the panel member.

Figure 43:
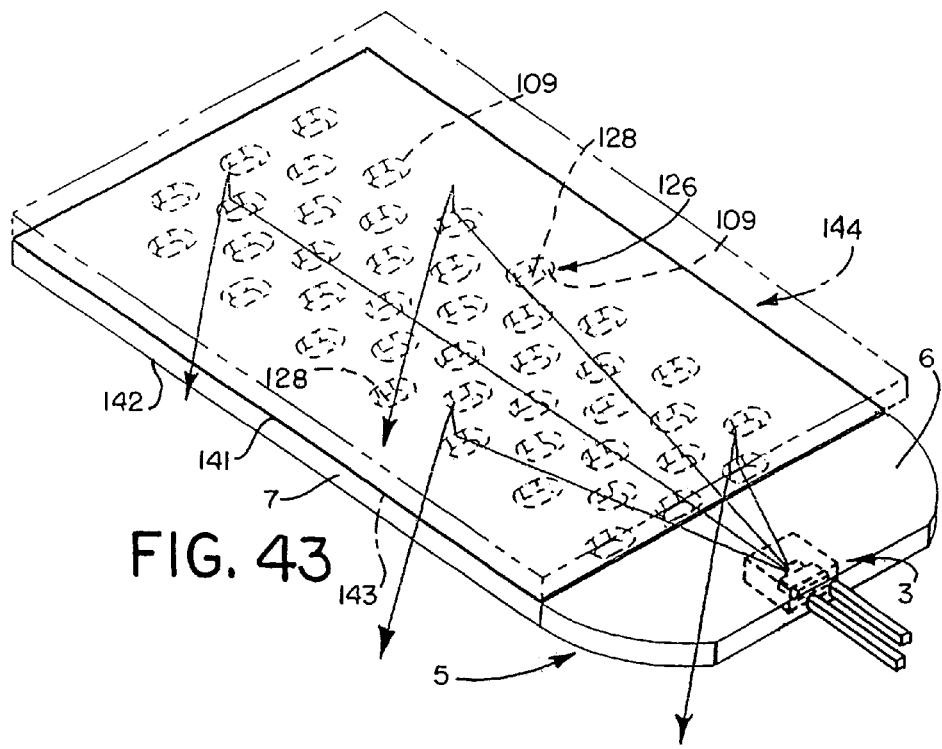
FIG. 43 is a schematic perspective view showing a light emitting panel assembly similar to FIG. 42 placed on a front face of a display to provide front lighting for the display.

FIG. 43 schematically shows the side 141 of the light emitting panel assembly 5 of FIG. 42 from which a majority of the light is emitted placed against the front face 143 of a liquid crystal display or other signage 144 for front lighting the display/signage when the ambient light is not sufficient for proper illumination. The portions of the panel member 7 overlying the display/signage 144 are transparent without any back reflector, whereby when the light source 3 is energized, light will be emitted from the side 141 of the panel member 7 contacting the front face 143 of the display/signage 144 and then reflected back out through the panel member 7 including particularly the planar surfaces 128 on the deformities.

By selecting the optical index of refraction of the panel member 7 to closely match the substrate of the display/signage 144, the light reflected by the display/signage will pass through the planar surfaces 128 of the deformities with minimal optical discontinuities for ease of viewing the display/ signage. Also, providing a random or variable pattern of light extracting deformities on the panel member insures that the spacing of the light extracting deformities does not match the pixel spacing of the display so as not to produce a headlight effect.

Because the light extracting deformities are of well defined shapes, the size, shape, location and orientation of each light extracting deformity can be individually adjusted or randomly varied at any given surface area of the panel member to spread the light output distribution uniformly across each panel surface area or obtain any other desired light output distribution at each panel surface area. Also, such light extracting deformities may be formed in or on any surface area of the panel member in any desired manner, such as by machining using a milling or laser cutter, or by molding or stamping or the like.

The light source 3 for the panel assemblies shown in FIGS. 16, 17 and 39 through 43 may be of any suitable type as previously described. However, preferably such light source is a focused light source such as a lens end bulb, a chip from an LED, or a laser or laser diode. Alternatively such light source may be an LED, incandescent lamp or other light source having an integral collector 145 (see FIG. 16) that collects the light from the light source and focuses the light. In either case the light from the light source is preferably focused in a predetermined pattern on the input surface 146 of the light transition area 6 which directs the light at an acceptable angle for entering the light input edge 18 of the light emitting panel 7 over a substantial portion of the cross sectional area of the panel.

Figure 44:
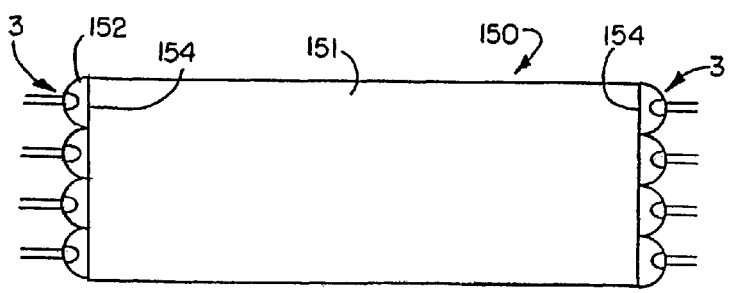

FIG. 44 schematically illustrates still another form of light emitting panel assembly 150 in accordance with this invention which is particularly adapted to be used for different types of phototherapy treatment by exposing various portions of the skin or eyes of a person to light being emitted from the panel assembly to treat such conditions as neonatal hyperbilirubinemia, insomnia, sleep disorders or tiredness associated with jet lag or shift work, certain types of psychiatric disorders such as seasonal affective disorder (SAD) and depression and so on. To that end, the light emitting panel assembly 150 includes a light emitting panel member 151 which may be in the shape of a pad or blanket. At one or both ends of the panel member 151 are one or more light transition areas 152 containing one or more LEDs or other light sources 3 for uniformly supplying light of any desired wavelength to the panel input edge 154 at one or both ends of the panel member. If desired, the light sources may be different colored LEDs so that the light from the LEDs can be mixed to produce virtually any desired colored light output distribution including white light from the panel member. Also, white LEDs may be used for producing a white light output distribution from the panel member.

Figure 45:
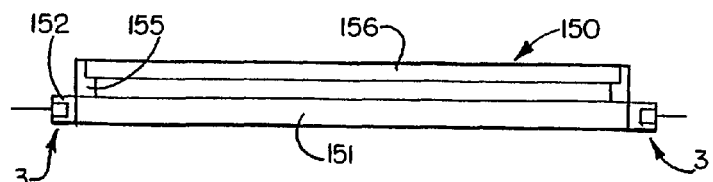

On one or more selected panel surface areas on one or both sides of the panel member 151 are a pattern of light extracting deformities or disruptions which are not shown in FIG. 44 but may be of any of the types previously described for producing a desired light output distribution from the panel surface areas. The portion of the body of a person to receive phototherapy treatment may be placed in close association with or directly against the light emitting surface areas of the panel. Alternatively, the panel assembly 150 may be provided with molded portions 155 at strategic locations on the panel member 151 (for example at all four corners) for providing structural support for locating other parts or components such as a diffuser or lens 156 as schematically shown in FIG. 45.

Figures 46, 47:
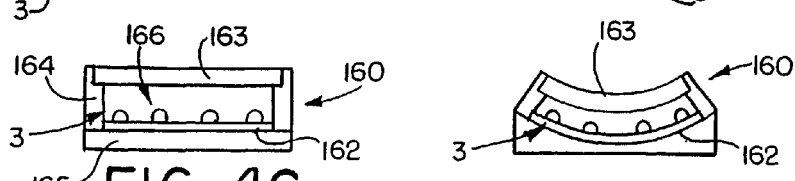

FIG. 46 shows still another form of light emitting panel assembly 160 in accordance with this invention for use in phototherapy treatment or other applications in which an array of LEDs or other light sources 3 are mounted on a printed circuit board 162 for directing light through a transparent member 163 which may be a diffuser or lens. The transparent member 163 is maintained in spaced apart relation from the printed circuit board 162 and light sources 3 mounted thereon by a plurality of upstanding supports 164 on a base 165 for the circuit board. Not only does this protect the circuit board 162 and light sources 3 against damage, but also provides an air gap 166 between the light sources 3 and transparent member 163 to facilitate dissipation of any heat that is produced by the light sources.

In FIG. 46 the circuit board 162 and transparent member 163 are shown as being substantially flat. However, it will be appreciated that such circuit board 162 and transparent member 163 may also be curved as schematically shown in FIG. 47 for supporting a body part such as an arm, leg or neck of a person receiving phototherapy treatment.

The various light emitting panel assemblies disclosed herein may be used for a great many different applications including for example liquid crystal display (LCD) or other signage back lighting or lighting in general, decorative and display lighting, automotive lighting, dental lighting, phototherapy or other medical lighting, membrane switch lighting, and sporting goods and apparel lighting or the like. Also the panel assemblies may be made such that the panel members and deformities are transparent without a back reflector. This allows the panel assemblies to be used for example to front light an LCD or other display such that the display is viewed through the transparent panel members in the manner previously described.

The pattern of the various optical deformities disclosed herein may also be varied in size, shape, density, placement, angle, rotation and/or type on or in one or more surface areas of a light emitting panel member to produce a desired light output distribution from the panel member to suit a particular application. By varying the pattern of optical deformities, the light output distribution can be made to be substantially uniform throughout all or a portion of the length of the panel member or variable to increase or decrease the brightness of one or more surface areas of the panel member.

Figure 48:
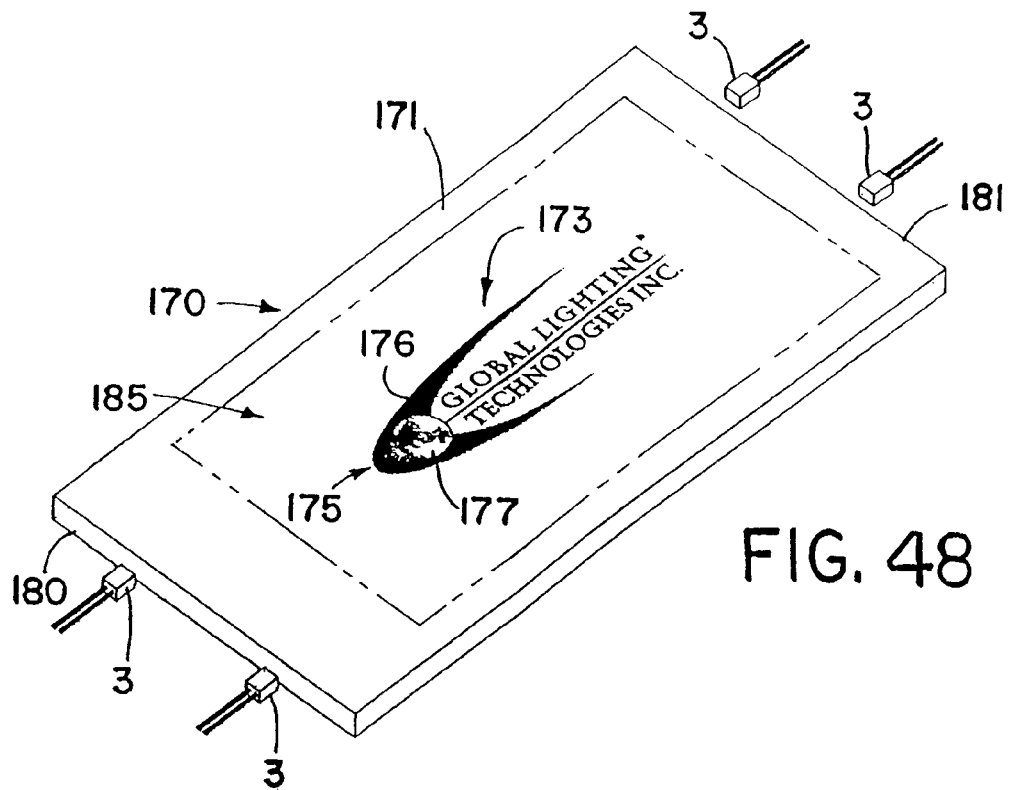
FIGS. 48 and 49 are schematic perspective views of other forms of light emitting panel assemblies in accordance with this invention having light output distributions in the form or shape of text, graphics, logo and/or image produced by variable patterns of individual optical deformities on or in the panel members.
Figure 49:
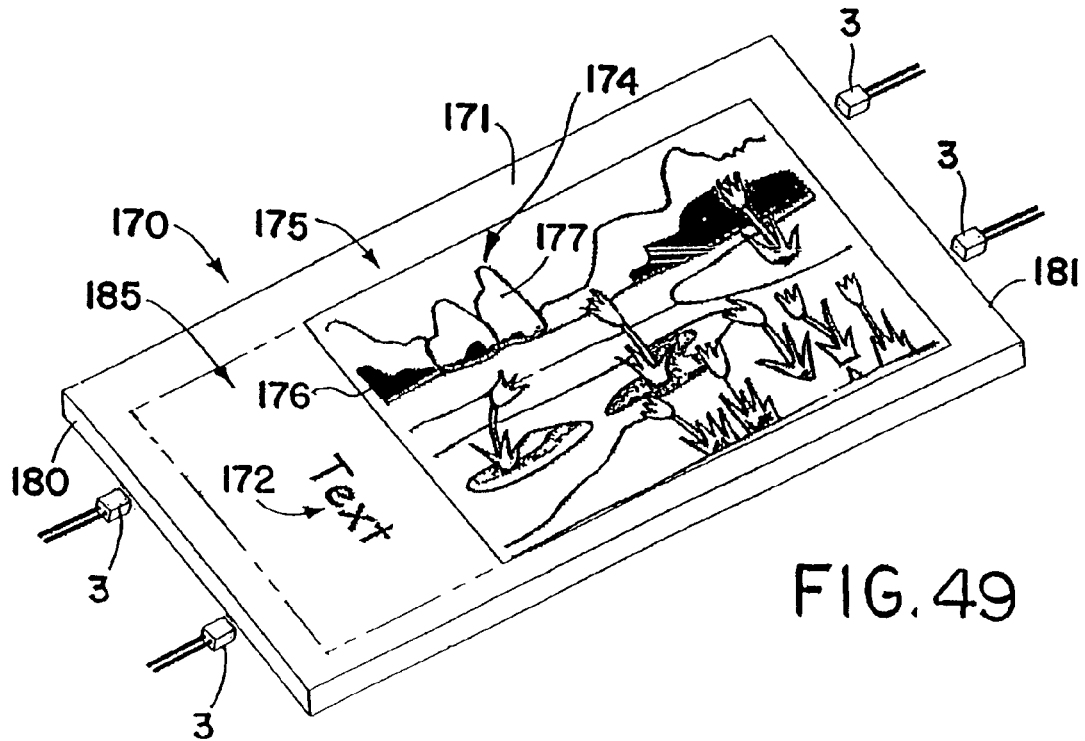

Also, by varying the pattern of optical deformities, the light output distribution of the panel member can be made to have more complicated features. For example, FIGS. 48 and 49 show light emitting panel assemblies 170 of the present invention in which the light output distribution of a specific area or areas of the light emitting panel members 171 may be in the form or shape of text 172, graphics or logo 173 and/or image 174 (hereafter individually or collectively referred to as a design/image 175). The dark and light areas shown in the light emitting regions in FIGS. 48 and 49 (as well as those shown in FIGS. 50-52) can be interpreted as either the higher light output areas or the lower light output areas. Also, the dark and light areas shown can have either a uniform light output from a given region, or a variable light output throughout the region such as a multi-level output distribution used to create a picture in an output distribution, for example. Moreover, the dark and light regions may have abrupt boundaries or the boundaries may be blended together so that there are no distinct boundaries between regions as desired. Generally any of the dark and light areas of FIGS. 48-52 may be interpreted in the above fashion.

The portions 176 of the design/image output distribution 175 that are relatively dark may be formed by surrounding the outline of the relatively dark portions with a suitable pattern of the optical deformities, whereas the portions 177 of the design/image output distribution 175 that are relatively bright (e.g., light) are shaped by placing a suitable pattern of the optical deformities in the shape of such relatively bright portions. Any desired variations in or uniformity of the intensity of the light output distribution of any portion of the design/image 175 may be obtained by varying the size, shape, density, placement, angle, rotation and/or type of the optical deformities.

The panel members may be lighted from one or more ends or sides by optically coupling one or more light sources to one or more input edges of the panel member. Panel members 171 of FIGS. 48 and 49 are shown being lighted by two light sources 3 optically coupled to input edges 180 and 181 adjacent each end of the panel members. However, it will be appreciated that any number and type of light sources may be used to light the panel members depending on the particular application.

The optical deformities may also be shaped or oriented to extract light propagating through the panel members preferentially in one direction over another. This allows different sets of optical deformities to be used to extract light in different preferred directions to construct any desired form or shape of design/image output distribution.

Different colored light sources may also be optically coupled to different input edges of the panel members so that the different sets of optical deformities will cause a preferred color of light to be emitted from the panel members. In this way, multi-colored output distributions can be created to suit a particular application. For example, if different colored light sources are optically coupled to the input edges 180 and 181 at opposite ends of the panel members 171, different sets of optical deformities may be shaped or oriented to extract light propagating through the panel members preferentially in one direction over another for causing the different colored light received by the different input edges to create a design/image output distribution that is multi-colored. In addition, by mixing the different sets of optical deformities within a given area, the light source colors may be mixed to produce colors in the output distribution that are different from the light source colors.

Figure 50:
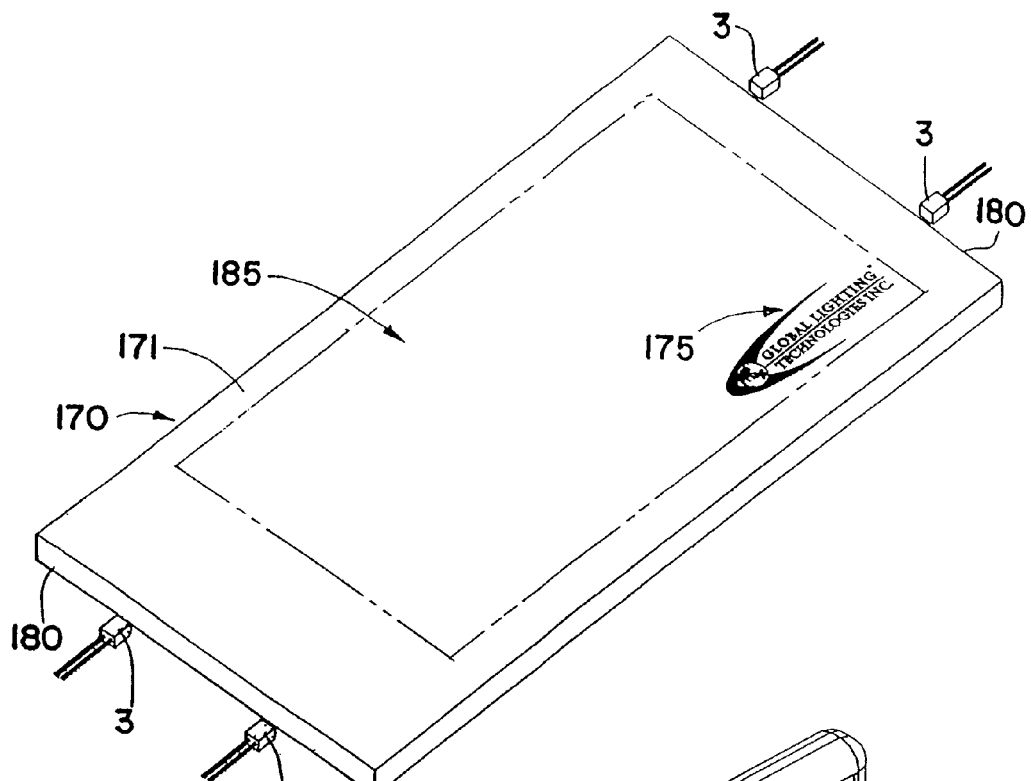
FIG. 50 is a schematic perspective view of another form of light emitting panel assembly including at least one light output distribution in the form or shape of text, graphics, logo and/or image located in another light output distribution to create a "watermark" or other effect.

The size of the design/image output distribution in relation to another light output distribution or distributions of the panel members may be varied as desired depending on the particular application. For example, FIGS. 48 and 49 show a design/image output distribution 175 that is relatively large in relation to another light output distribution 185 of the panel members, whereas FIG. 50 shows a design/image output distribution 175 that is relatively small in relation to another light output distribution 185 of the panel member.

Figure 51:
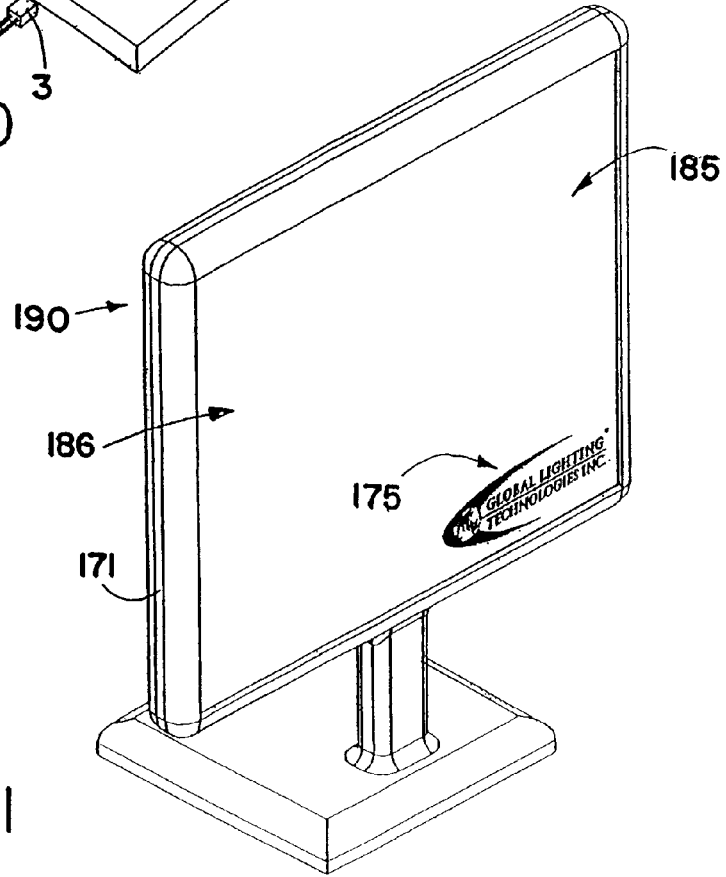
FIG. 51 is a schematic perspective view of an optical assembly in accordance with this invention including a screen display that is backlighted for example by the light emitting panel assembly of FIG. 50 with the text, graphics, logo and/or image output distribution of the backlight visible for example in a corner of the display.

Making the design/image relatively small will permit the design/image output distribution to be placed wherever desired in another output distribution of the panel member (which may, for example, be uniform) to create a watermark, logo, security marking, label or other effect in the other output distribution. For example, the panel member 171 of FIG. 50 may be used to backlight a display 186 such as a liquid crystal display of an optical assembly 190 as shown in FIG. 51. If the design/image output distribution 175 of the panel member 171 is placed in a corner of the panel member as shown in FIG. 50, the design/image will be viewable in a corner of the display 86 as shown in FIG. 51 to create, for example, a "corporate presence" on the display without obscuring images or other data being displayed on the display.

Figure 52:
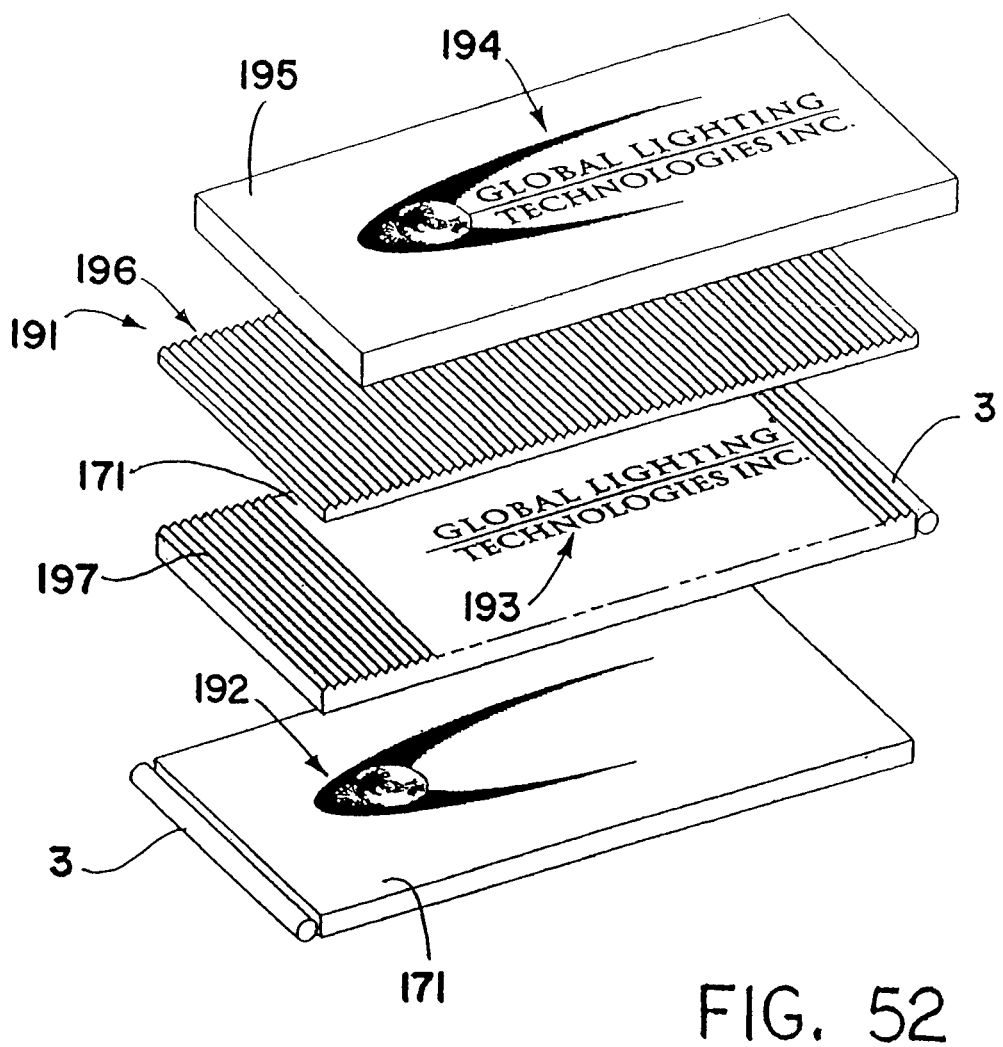
FIG. 52 is an exploded perspective view of another form of optical assembly in accordance with this invention including two or more light emitting panel assemblies in overlying relation to one another each having different light output distributions that produce one or more parts of a more complex output distribution in the form or shape of text, graphics, logo and/or image that is visible through the panel members and/or an optical film and/or a display overlying the panel members when viewed therethrough.

An optical assembly may also be comprised of multiple light emitting panel members overlying one another, each having a different light output distribution or color that produces one or more portions or parts of a more complicated light output distribution or an image with more than one dimension. One such optical assembly 191 is schematically shown in FIG. 52, and includes two (or more) light emitting panel members 171, each having a different light output distribution 192, 193 that produces a portion of the total design/image output distribution 194 that can be seen when viewed through both panel members or through a display 195 overlying the panel members. The term display as used herein may include, for example, one or more liquid crystal displays, optical films, diffusers, touch pads, and/or transparent or semi-transparent overlays or covers and the like.

The intensity of the light output distribution of each of the panel members 171 may be different to create a multi-intensity composite light output distribution when viewed through the panel members or the display. Also, since each of the panel members may have its own light source or light sources 3, different colored light sources may be used for each panel member to produce a different colored light output distribution for each panel member which when viewed through both panel members or a display overlying the panel members will produce a multi-colored composite light output distribution 194.

One or more transparent brightness enhancement films, light management films, diffuser films, color filters or other films 196 may also be attached or positioned in close proximity to the side or sides of the panel members from which the emitted light is viewed to produce a desired effect. For example, the films 196 may be light redirecting films or light management films having optical deformities that redistribute the light passing through the films such that the distribution of light exiting the films is directed more normal to the surface of the films. Also the films 196 may be color filters or diffusers having for example prismatic or lenticular deformities on or in the films that allow different light output distributions to be seen when the panel members are viewed through the films (and the display) from different angles. Other optical deformities 197 such as prismatic or lenticular optical deformities may also be provided on the side of the panel member or members 171 opposite the side on which the pattern of optical deformities is provided as further schematically shown in FIG. 52 to allow different light output distributions to be seen when the panel member or members are viewed through the other optical deformities from different angles.

Although the invention has been shown and described with respect to certain preferred embodiments, it is obvious that equivalent alterations and modifications will occur to others skilled in the art upon the reading and understanding of the specification. In particular, with regard to the various functions performed by the above-described components, the terms (including any reference to a "means") used to describe such components are intended to correspond, unless otherwise indicated, to any component which performs the specified function of the described component (e.g., that is functionally equivalent), even though not structurally equivalent to the disclosed component which performs the function of the invention. In addition, while a particular feature of the invention may have been disclosed with respect to only one of several embodiments, such feature may be combined with one or more other features of the other embodiments as may be desired and advantageous for any given or particular application.

What is claimed is:

1. An optical assembly comprising light sources and a light emitting panel member, the light emitting panel member comprising:

opposite sides, one of the sides comprising a light emitting surface area;

an input edge for receiving light from the light sources for propagating the light through the panel member in one direction, each of the light sources being optically coupled to a different location along the input edge; and a pattern of individual optical deformities on or in at least one of the sides of the panel member for creating a light output distribution from the light emitting surface area, the individual optical deformities being varied throughout the pattern, different sets of the optical deformities within the pattern each having at least one surface that is shaped or oriented to extract light propagating in the one direction through the panel member in respective different directions for viewing from respective different angles through the one of the sides of the panel member, wherein the individual optical deformities that create at least one of the light output distributions are varied to create a design/image output distribution.

2. An optical assembly comprising light sources and a light emitting panel member, the light emitting panel member comprising:

opposite sides, one of the sides comprising a light emitting surface area;

an input edge for receiving light from the light sources, each of the light sources being optically coupled to a different location along the input edge; and a pattern of individual optical deformities on or in at least one of the sides of the panel member for creating a generally uniform field of light output distribution from the light emitting surface area except in one or more different regions within the generally uniform field of light output distribution where the individual optical deformities are varied throughout the pattern to create one or more different light output distributions from the one or more different regions of the light emitting surface area.

3. The optical assembly of claim 2, wherein one of the different light output distributions is relatively large in relation to another of the different light output distributions.

4. A light emitting assembly comprising:

a light guide having opposite sides and first and second opposing light input edges;

a first set of light sources optically coupled to one of the light input edges for propagating light through the light guide in one direction;

a second set of light sources optically coupled to the other light input edge for propagating light through the light guide in a direction opposite the one direction;

and first and second sets of optical deformities on or in at least one of the sides of the light guide for creating a light output distribution from the light guide;

wherein the optical deformities of one of the sets are shaped or oriented for extracting light from the light guide entering through one of the light input edges preferentially in a first direction; and the optical deformities of the other set are shaped or oriented for extracting light from the light guide entering through the other light input edge preferentially in a second direction that is different from the first direction.

5. The light emitting assembly of claim 4 wherein the light sources of one of the sets are of a different color than the light sources of the other set.

6. The light emitting assembly of claim 5 wherein the optical deformities of both sets are shaped or oriented to create a multi-colored design/image light output distribution from the light guide.

7. The light emitting assembly of claim 4 wherein the optical deformities of both sets are mixed together on or in at least one of the sides of the light guide.

8. The light emitting assembly of claim 4 further comprising a light redirecting film in overlying relation to at least one of the sides of the light guide from which light is emitted for redirecting the emitted light.

9. The light emitting assembly of claim 4 wherein the optical deformities of at least one of the sets have at least one surface that is shaped or oriented to extract light from the light guide entering through at least one of the light input edges in respective different directions for viewing from respective different angles through one of the sides of the light guide.

10. The light emitting assembly of claim 9 wherein the optical deformities of at least one of the sets are varied to create a design/image output distribution from the light guide.

11. The light emitting assembly of claim 4 wherein one of the sides comprises a light emitting surface area, and a pattern of the optical deformities of at least one of the sets create a generally uniform field of light output distribution from the light emitting surface area except in one or more different regions within the generally uniform field of light output distribution where the optical deformities of at least one of the sets are varied throughout the pattern to create one or more different light output distributions from the one or more different regions of the light emitting surface area.

12. The light emitting assembly of claim 11, wherein one of the different light output distributions is relatively large in relation to another of the different light output distributions.

* * * * *